(12) United States Patent
Rosenthal et al.

(10) Patent No.: US 12,186,409 B2
(45) Date of Patent: *Jan. 7, 2025

(54) METHODS OF SCREENING FOR SORTILIN BINDING ANTAGONISTS

(71) Applicant: Alector LLC, South San Francisco, CA (US)

(72) Inventors: Arnon Rosenthal, Woodside, CA (US); Tina Schwabe, San Francisco, CA (US)

(73) Assignee: ALECTOR LLC, South San Francisco, CA (US)

( * ) Notice: Subject to any disclaimer, the term of this patent is extended or adjusted under 35 U.S.C. 154(b) by 836 days.

This patent is subject to a terminal disclaimer.

(21) Appl. No.: 17/088,237

(22) Filed: Nov. 3, 2020

(65) Prior Publication Data

US 2021/0121583 A1   Apr. 29, 2021

Related U.S. Application Data

(62) Division of application No. 15/565,063, filed as application No. PCT/US2016/026485 on Apr. 7, 2016, now Pat. No. 10,849,992.

(60) Provisional application No. 62/144,277, filed on Apr. 7, 2015.

(51) Int. Cl.
| | | |
|---|---|---|
| G01N 33/543 | (2006.01) | |
| A61K 49/00 | (2006.01) | |
| C07K 16/28 | (2006.01) | |
| G01N 21/64 | (2006.01) | |
| G01N 33/533 | (2006.01) | |
| G01N 33/542 | (2006.01) | |

(52) U.S. Cl.
CPC ...... *A61K 49/0056* (2013.01); *C07K 16/2863* (2013.01); *G01N 21/6428* (2013.01); *G01N 33/533* (2013.01); *G01N 33/542* (2013.01); *G01N 2333/705* (2013.01); *G01N 2500/02* (2013.01); *G01N 2500/10* (2013.01)

(58) Field of Classification Search
None
See application file for complete search history.

(56) References Cited

U.S. PATENT DOCUMENTS

| | | |
|---|---|---|
| RE30,985 E | 6/1982 | Cartaya |
| 4,560,655 A | 12/1985 | Baker |
| 4,657,866 A | 4/1987 | Kumar |
| 4,767,704 A | 8/1988 | Cleveland et al. |
| 4,816,567 A | 3/1989 | Cabilly et al. |
| 4,927,762 A | 5/1990 | Darfler |
| 5,122,469 A | 6/1992 | Mather et al. |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 8,008,009 B2 | 8/2011 | Choquet-Kastylevsky et al. |
| 8,066,997 B2 | 11/2011 | Nykjaer et al. |
| 8,460,657 B2 | 6/2013 | Nykjaer et al. |
| 8,703,125 B2 | 4/2014 | Pedersen et al. |
| 8,748,384 B2 | 6/2014 | Andersen et al. |
| 8,795,627 B2 | 8/2014 | Starr et al. |
| 8,815,808 B2 | 8/2014 | Nykjaer et al. |
| 8,877,714 B2 | 11/2014 | Starr et al. |
| 8,986,690 B2 | 3/2015 | Nykjaer et al. |
| 9,061,045 B2 | 6/2015 | Choquet-Kastylevsky et al. |
| 9,062,126 B2 | 6/2015 | Zankel et al. |
| 9,084,745 B2 | 7/2015 | Nykjaer et al. |
| 9,234,036 B2 | 1/2016 | Anderson et al. |
| 9,605,073 B2 | 3/2017 | Nykjaer et al. |
| 9,670,263 B2 | 6/2017 | Pedersen et al. |
| 9,822,366 B2 | 11/2017 | Aikawa et al. |
| 10,221,438 B2 * | 3/2019 | Gosselin .............. C07K 14/435 |
| 10,849,992 B1 | 12/2020 | Rosenthal et al. |

(Continued)

FOREIGN PATENT DOCUMENTS

| | | |
|---|---|---|
| WO | WO1987000195 A1 | 1/1987 |
| WO | WO1987004462 A1 | 7/1987 |
| WO | WO1990003430 A1 | 4/1990 |
| WO | WO1991010741 A1 | 7/1991 |
| WO | WO1996033735 A1 | 10/1996 |
| WO | WO1996034096 A1 | 10/1996 |
| WO | WO1998024893 A1 | 6/1998 |
| WO | WO2004056385 A2 | 7/2004 |
| WO | WO2005044293 A2 | 5/2005 |
| WO | WO2006138343 A2 | 12/2006 |

(Continued)

OTHER PUBLICATIONS

Xu et al., A bioluminescence resonance energy transfer (BRET) system: Application to interacting circadian clock proteins, Proc. Natl. Acad. Sci, vol. 96, 1999, pp. 151-156. (Year: 1999).*

(Continued)

*Primary Examiner* — Gary Counts
(74) *Attorney, Agent, or Firm* — MORRISON & FOERSTER LLP

(57) ABSTRACT

The present disclosure provides methods of screening for a sortilin binding antagonist. In some embodiments, the methods include incubating an agent with a sortilin protein and a sortilin ligand, where the sortilin protein and sortilin ligand are each attached to a member of a fluorescence donor/acceptor pair, exciting the fluorescence donor of the fluorescence donor/acceptor pair, and detecting fluorescence emitted by the fluorescence donor at a second wavelength and fluorescence emitted by the fluorescence acceptor at a third wavelength. A decrease in the ratio of the fluorescence emitted by the fluorescence acceptor at the third wavelength to the fluorescence emitted by the fluorescence donor at the second wavelength, as compared to the ratio in the absence of the agent, indicates that the agent is a sortilin binding antagonist.

16 Claims, 16 Drawing Sheets

Specification includes a Sequence Listing.

(56) References Cited

U.S. PATENT DOCUMENTS

| | | | |
|---|---|---|---|
| 2003/0003444 | A1 | 1/2003 | Pelletier et al. |
| 2005/0096516 | A1 | 5/2005 | Soykan et al. |
| 2008/0213270 | A1 | 9/2008 | Piliponsky et al. |
| 2009/0068200 | A1 | 3/2009 | Choquet-Kastylevsky et al. |
| 2009/0220988 | A1 | 9/2009 | Trinquet |
| 2010/0028333 | A1 | 2/2010 | Getty et al. |
| 2010/0105034 | A1 | 4/2010 | Hutton et al. |
| 2011/0104666 | A1 | 5/2011 | Matsubara et al. |
| 2011/0166036 | A1 | 7/2011 | Nykjaer et al. |
| 2012/0039865 | A1 | 2/2012 | Strittmatter et al. |
| 2012/0315244 | A1 | 12/2012 | Yuan et al. |
| 2013/0115222 | A1 | 5/2013 | Hempstead et al. |
| 2013/0171173 | A1 | 7/2013 | Choquet-Kastylevsky et al. |
| 2013/0336988 | A1 | 12/2013 | Hempstead et al. |
| 2014/0004108 | A1 | 1/2014 | Yuan et al. |
| 2014/0038942 | A1* | 2/2014 | Karstens .................. A61P 5/16 |
| | | | 548/362.5 |
| 2015/0299304 | A1 | 10/2015 | Nykjaer et al. |
| 2015/0368231 | A1 | 12/2015 | Maltas et al. |
| 2016/0024172 | A1 | 1/2016 | Zankel et al. |
| 2016/0060346 | A1 | 3/2016 | Andersen et al. |
| 2016/0159871 | A1* | 6/2016 | Zecri .................. A61K 47/6811 |
| | | | 514/6.9 |
| 2016/0194631 | A1 | 7/2016 | Yuan et al. |
| 2016/0349276 | A1 | 12/2016 | Jepsen et al. |
| 2017/0049855 | A1 | 2/2017 | Liu et al. |
| 2017/0096486 | A1 | 4/2017 | Landberg |
| 2017/0158766 | A1 | 6/2017 | Nykjaer et al. |
| 2017/0210808 | A1 | 7/2017 | Rosenthal et al. |
| 2017/0240611 | A1 | 8/2017 | Pedersen et al. |
| 2017/0246263 | A1 | 8/2017 | Concino et al. |
| 2017/0247391 | A1 | 8/2017 | Grembecka et al. |
| 2017/0267761 | A1 | 9/2017 | Biilmann Ronn et al. |
| 2017/0318057 | A1 | 11/2017 | Nykjaer et al. |

FOREIGN PATENT DOCUMENTS

| | | |
|---|---|---|
| WO | WO2007035716 A2 | 3/2007 |
| WO | WO2007088305 A1 | 8/2007 |
| WO | WO2008036682 A2 | 3/2008 |
| WO | WO2008052016 A2 | 5/2008 |
| WO | WO2008074329 A2 | 6/2008 |
| WO | WO2008076262 A2 | 6/2008 |
| WO | WO2008086452 A2 | 7/2008 |
| WO | WO2009140972 A2 | 11/2009 |
| WO | WO2009155932 A2 | 12/2009 |
| WO | WO2010022175 A1 | 2/2010 |
| WO | WO2010028333 A2 | 3/2010 |
| WO | WO2010069331 A2 | 6/2010 |
| WO | WO2011041582 A2 | 4/2011 |
| WO | WO2011159762 A1 | 12/2011 |
| WO | WO2012068332 A2 | 5/2012 |
| WO | WO2014071131 A1 | 5/2014 |
| WO | WO2015119989 A1 | 8/2015 |
| WO | WO2015121166 A1 | 8/2015 |
| WO | WO2015144860 A1 | 10/2015 |
| WO | WO2016025523 A1 | 2/2016 |
| WO | WO2016164608 A1 | 10/2016 |
| WO | WO2016164637 A1 | 10/2016 |
| WO | WO2017009327 A1 | 1/2017 |
| WO | WO2017024137 A1 | 2/2017 |

OTHER PUBLICATIONS

Diamandis et al., Immunoassay, Academic Press, Chapter 11, The Avidin-Biotin System, pp. 237-267, 1996. (Year: 1996).*
Andersen et al., "Identification of the First Small-Molecule Ligand of the Neuronal Receptor Sortilin and Structure Determination of the Receptor-Ligand Complex", Acta Crystallographica Section D Biological Crystallography, vol. 70, 2014, pp. 451-460.
Baker et al., "Mutations in Progranulin Cause Tau-Negative Frontotemporal Dementia Linked to Chromosome 17", Nature, vol. 442, Aug. 24, 2006, pp. 916-919.
Barnes et al., "Methods for Growth of Cultured Cells in Serum-Free Medium", Analytical Biochemistry, vol. 102, 1980, pp. 255-270.
Brouwers et al., "Genetic Variability in Progranulin Contributes to Risk for Clinically Diagnosed Alzheimer Disease", Neurology, vol. 71, 2008, pp. 656-664.
Carecchio et al., "Cerebrospinal Fluid Biomarkers in Progranulin Mutations Carriers", Journal of Alzheimer's Disease, vol. 27, 2011, pp. 781-790.
Carrasquillo et al., "Genome-wide Screen Identifies rs646776 near Sortilin as a Regulator of Progranulin Levels in Human Plasma", The American Journal of Human Genetics, vol. 87, Dec. 10, 2010, pp. 890-897.
Chen et al., "Sortilin Controls Intracellular Sorting of Brain-Derived Neurotrophic Factor to the Regulated Secretory Pathway", The Journal of Neuroscience, vol. 25, No. 26, Jun. 29, 2005, pp. 6156-6166.
Clackson et al., "Making Antibody Fragments Using Phage Display Libraries", Nature, vol. 352, Aug. 15, 1991, pp. 624-628.
Cruts et al., "Loss of Progranulin Function in Frontotemporal Lobar Degeneration", Trends Genetics, vol. 24, No. 4, 2008, pp. 186-194.
Degorce et al., "HTRF: A Technology Tailored for Drug Discovery—A Review of Theoretical Aspects and Recent Applications", Current Chemical Genomics, vol. 3, 2009, pp. 22-32.
Egashira et al., "The Growth Factor Progranulin Attenuates Neuronal Injury Induced by Cerebral Ischemia-Reperfusion Through the Suppression of Neutrophil Recruitment", Journal of Neuroinflammation, vol. 10, No. 105, 2013, pp. 1-13.
Fellouse et al., "Synthetic Antibodies from a Four-Amino-Acid Code: A Dominant Role for Tyrosine in Antigen Recognition", PNAS, vol. 101, No. 34, Aug. 24, 2004, pp. 12467-12472.
Fishwild et al., "High-Avidity Human IgGK Monoclonal Antibodies from a Novel Strain of Minilocus Transgenic Mice", Nature Biotechnology, vol. 14, Jul. 1996, pp. 845-851.
Galimberti et al., "GRN Variability Contributes to Sporadic Frontotemporal Lobar Degeneration", Journal of Alzheimer's Disease, vol. 19, 2010, pp. 171-177.
Gerngross, Tillman U., "Advances in the Production of Human Therapeutic Proteins in Yeasts and Filamentous Fungi", Nature Biotechnology, vol. 22, No. 11, Nov. 2004, pp. 1409-1414.
Graham et al., "Characteristics of a Human Cell Line Transformed by DNA from Human Adenovirus Type 5", Journal of General Virology, vol. 36, 1977, pp. 59-72.
Ham et al., "Media and Growth Requirements", Methods in Enzymology, vol. LVIII, 1979, pp. 44-93.
Hongo et al., "Development and Characterization of Murine Monoclonal Antibodies to the Latency-Associated Peptide of Transforming Growth Factor β1", Hybridoma, vol. 14, No. 3, 1995, pp. 253-260.
Hu et al., "Sortilin-Mediated Endocytosis Determines Levels of the Frontotemporal Dementia Protein, Progranulin", Neuron, vol. 68, Nov. 18, 2010, pp. 654-667.
Jakobovits et al., "Analysis of Homozygous Mutant Chimeric Mice: Deletion of The Immunoglobulin Heavy-chain Joining Region Blocks B-Cell Development and Antibody Production", Proceedings of the National Academy of Sciences, vol. 90, Mar. 1993, pp. 2551-2555.
Jakobovits et al., "Germ-line Transmission and Expression of a Human-derived Yeast Artificial Chromosome", Nature, vol. 362, Mar. 18, 1993, pp. 255-258.
Kohler et al., "Continuous Cultures of Fused Cells Secreting Antibody of Predefined Specificity", Nature, vol. 256, Aug. 7, 1975, pp. 495-497.
Laird et al., "Progranulin is Neurotrophic in Vivo and Protects against a Mutant TDP-43 Induced Axonopathy", PLoS ONE, vol. 5, No. 10, Oct. 2010, pp. 1-7.
Lee et al., "Bivalent Antibody Phage Display Mimics Natural Immunoglobulin", Journal of Immunological Methods, vol. 284, 2004, pp. 119-132.
Lee et al., "High-affinity Human Antibodies from Phage-displayed Synthetic Fab Libraries with a Single Framework Scaffold", Journal of Molecular Biology, vol. 340, 2004, pp. 1073-1093.

(56) References Cited

OTHER PUBLICATIONS

Lee et al., "Targeted Manipulation of the Sortilin-Progranulin Axis Rescues Progranulin Haploinsufficiency", Human Molecular Genetics, vol. 23, No. 6, 2014, pp. 1467-1478.
Li et al., "Optimization of Humanized IgGs in Glycoengineered Pichia Pastoris", Nature Biotechnology, vol. 24, No. 2, Feb. 2006, pp. 210-215.
Lonberg et al., "Antigen-Specific Human Antibodies from Mice Comprising Four Distinct Genetic Modifications", Nature, vol. 368, Apr. 28, 1994, pp. 856-859.
Lonberg et al., "Human Antibodies from Transgenic Mice", International Reviews of Immunology. vol. 13, 1995, pp. 65-93.
Marchetti et al., "Ligand-Induced Dynamics of Neurotrophin Receptors Investigated by Single-Molecule Imaging Approaches", International Journal of Molecular Sciences, vol. 16, 2015, pp. 1949-1979.
Marks et al., "By-Passing Immunization: Building High Affinity Human Antibodies By Chain Shuffling", Biotechnology, vol. 10, Jul. 1992, pp. 779-783.
Marks et al., "By-passing Immunization: Human Antibodies from V-gene Libraries Displayed on Phage", Journal of Molecular Biology, vol. 222, 1991, pp. 581-597.
Martens et al., "Progranulin Deficiency Promotes Neuroinflammation and Neuron Loss Following Toxin-Induced Injury", The Journal of Clinical Investigation, vol. 122, No. 11, Nov. 2012, pp. 3955-3959.
Mather et al., "Culture of Testicular Cells in Hormone-Supplemented Serum-Free Medium", Annals of the New York Academy of Sciences, Testicular Cell Culture, 1982, pp. 44-68.
Mather, Jennie P., "Establishment and Characterization of Two Distinct Mouse Testicular Epithelial Cell Lines", Biology of Reproduction, vol. 23, 1980, pp. 243-252.
Mazella et al., "Spadin, a Sortilin-Derived Peptide, Targeting Rodent TREK-1 Channels: A New Concept in the Antidepressant Drug Design", PLoS Biology, vol. 8, No. 4, Apr. 2010, pp. 1-17.
Mazella, et al., "The 100-kDa Neurotensin Receptor Is gp95/Sortilin, A Non-G-Protein-coupled Receptor", The Journal of Biological Chemistry, vol. 273, No. 41, Oct. 9, 1998., pp. 26273-26276.
Morrison, Sherie L., "Success in specification", Nature, vol. 368, Apr. 28, 1994, pp. 812-813.
Neuberger, Michael, "Generating high-avidity human Mabs in mice", Nature Biotechnology, vol. 14, Jul. 1996, pp. 826.
Nykjaer et al., "Sortilin is Essential for proNGF Induced Neuronal Cell Death", Nature, vol. 427, Feb. 26, 2004, pp. 843-848.
Nykjaer et al., "Sortilin: A Receptor to Regulate Neuronal Viability and Function", Trends in Neurosciences, vol. 35, No. 4, Apr. 2012, pp. 261-270.
Petersen et al., "Propeptide Cleavage Conditions Sortilin/Neurotensin Receptor-3 for Ligand Binding", The EMBO Journal, vol. 18, No. 3, 1999, pp. 595-604.
Pickford et al., "Progranulin Is a Chemoattractant for Microglia and Stimulates Their Endocytic Activity", The American Journal of Pathology, vol. 178, No. 1, Jan. 2011, pp. 284-295.
Quistgaard et al., "Ligands Bind to Sortilin in the Tunnel of a Ten-Bladed β-Propeller Domain", Nature Structural & Molecular Biology, vol. 16, No. 1, Jan. 2009, pp. 96-98.
Schrøder et al., "The Identification of AF38469: An Orally Bioavailable Inhibitor of the VPS10P Family Sorting Receptor Sortilin", Bioorganic & Medicinal Chemistry Letters, vol. 24, 2014, pp. 177-180.
Sheng et al., "Progranulin Polymorphism rs5848 is Associated with Increased Risk of Alzheimer's Disease", Gene, vol. 542, 2014, pp. 141-145.
Sidhu et al., "Phage-displayed Antibody Libraries of Synthetic Heavy Chain Complementarity Determining Regions", Journal of Molecular Biology, vol. 338, Issue 2, Apr. 2004, pp. 299-310.
Sun et al., "FRET Microscopy in 2010: The legacy of Theodor Förster on the 100th Anniversary of his Birth", Chemphyschem, vol. 12 No. 3, Feb. 25, 2011, pp. 462-474.
Tang et al., "The Growth Factor Progranulin Binds to TNF Receptors and Is Therapeutic against Inflammatory Arthritis in Mice", Science, vol. 332, Apr. 22, 2011, pp. 478-484.
Tao et al., "Neuroprotective Effects of Progranulin in Ischemic Mice", Brain Research, vol. 1436, 2012, pp. 130-136.
Ullman et al., "Luminescent Oxygen Channeling Immunoassay: Measurement of Particle Binding Kinetics By Chemiluminescence", Proceedings of the National Academy of Sciences, vol. 91, Jun. 1994, pp. 5426-5430.
Urlaub et al., "Isolation of Chinese Hamster Cell Mutants Deficient in Dihydrofolate Reductase Activity", Proceedings of the National Academy of Sciences, vol. 77, No. 7, Jul. 1980, pp. 4216-4220.
Van Kampen et al., "Progranulin Gene Delivery Protects Dopaminergic Neurons in a Mouse Model of Parkinson's Disease", PloS One, vol. 9, No. 5, 2014, pp. 1-10.
Yano et al., "Proneurotrophin-3 Is a Neuronal Apoptotic Ligand: Evidence for Retrograde-Directed Cell Killing", The Journal of Neuroscience, vol. 29, No. 47, Nov. 25, 2009, pp. 14790-14802.
Yin et al., "Exaggerated Inflammation, Impaired Host Defense, and Neuropathology in Progranulin-Deficient Mice", The Journal of Experimental Medicine, vol. 207, No. 1, Jan. 2010, pp. 117-128.
Zheng et al., "C-Terminus of Progranulin Interacts with the Beta-Propeller Region of Sortilin to Regulate Progranulin Trafficking", PLoS One, vol. 6, Issue 6, Jun. 2011, 7 pages.
International Preliminary Report on Patentability received for PCT Patent Application No. PCT/US2016/026485, mailed on Oct. 19, 2017, 10 pages.
International Search Report and Written received for PCT Patent Application No. PCT/US2016/026485, mailed on Jul. 26, 2016, 13 pages.

\* cited by examiner

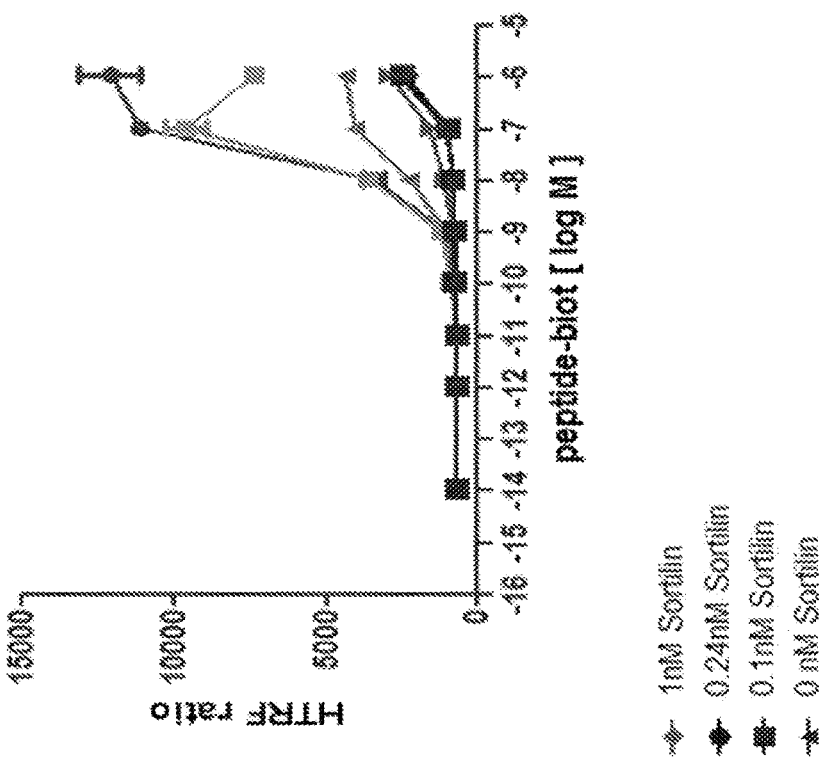
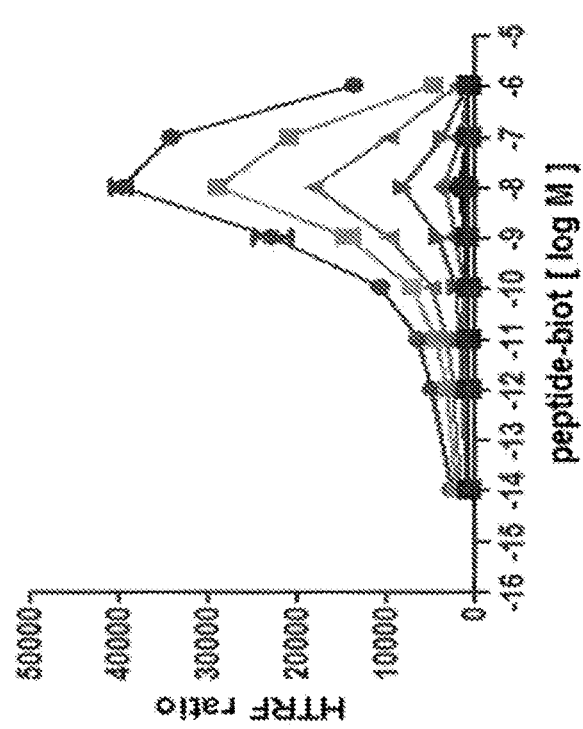
FIG. 3A
FIG. 3B

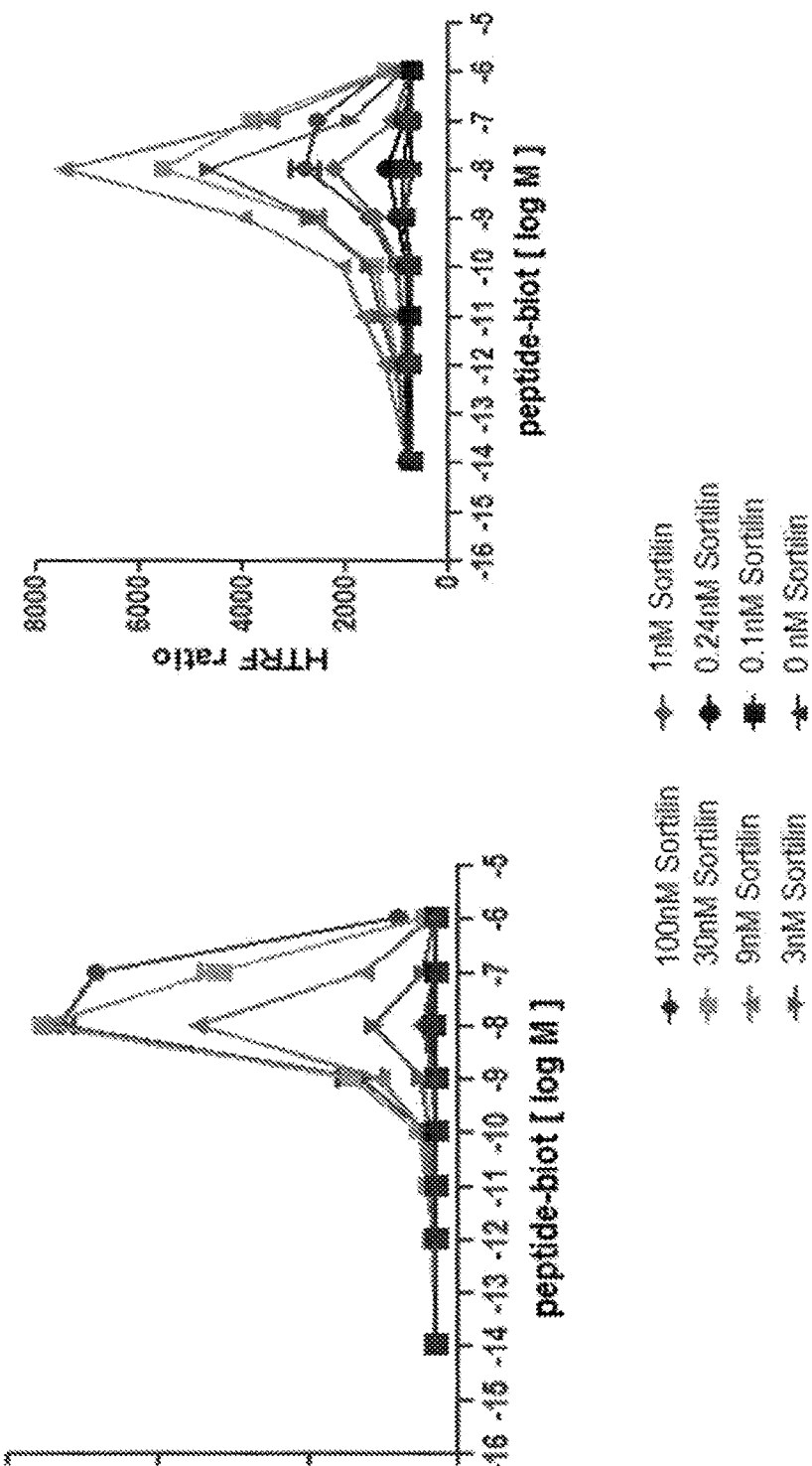

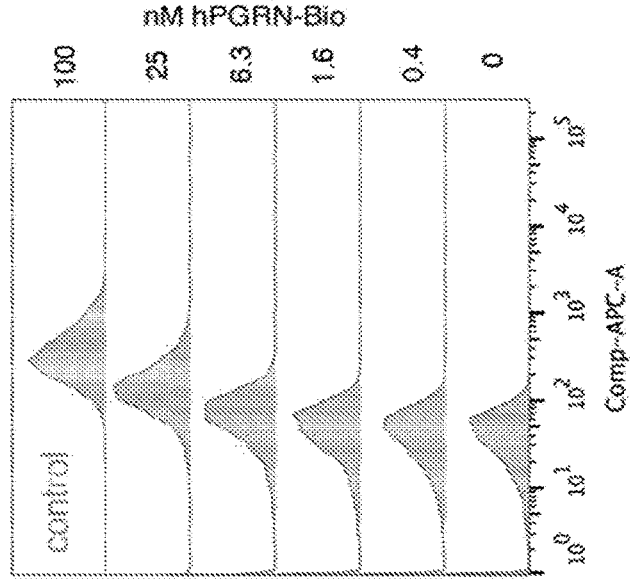
FIG. 7A
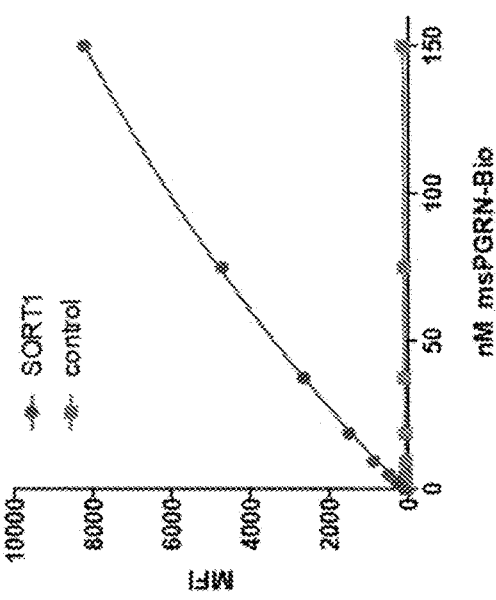
FIG. 7C
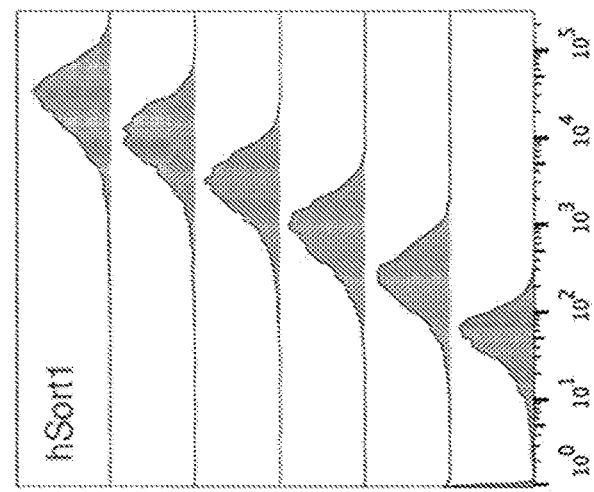
FIG. 7B
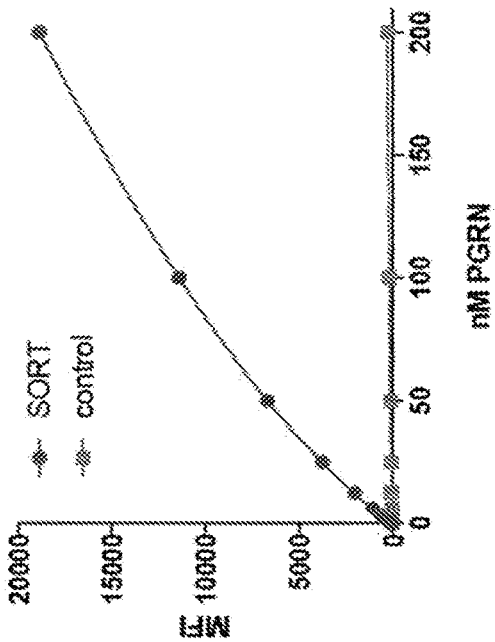

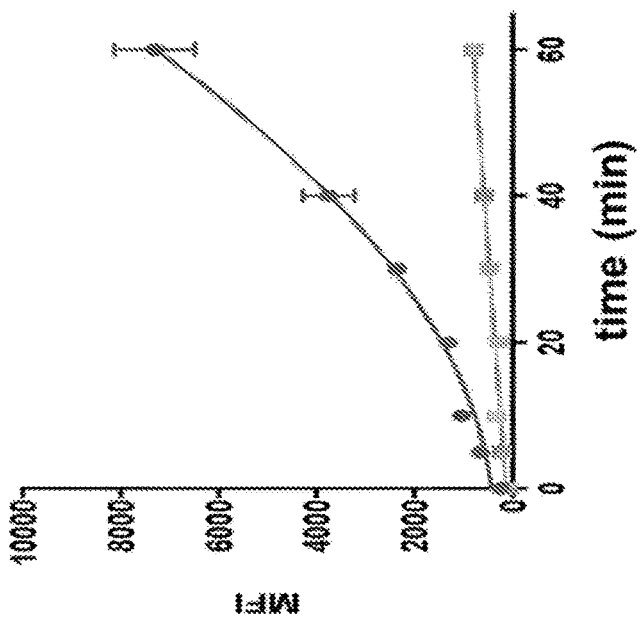
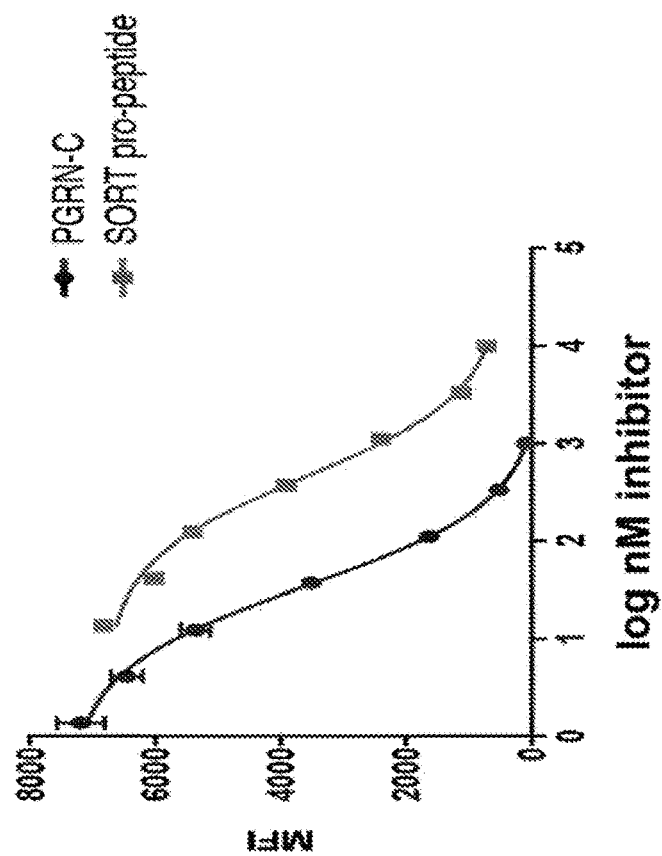
FIG. 10A
FIG. 10B

METHODS OF SCREENING FOR SORTILIN BINDING ANTAGONISTS

CROSS-REFERENCE TO RELATED APPLICATIONS

This application is a divisional of U.S. application Ser. No. 15/565,063, filed Oct. 6, 2017, now U.S. Pat. No. 10,849,992, issued Dec. 1, 2020, which is a U.S. national phase patent application of PCT/US2016/026485, filed Apr. 7, 2016, which claims the benefit of U.S. Provisional Application No. 62/144,277, filed Apr. 7, 2015, each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 735022000510SEQLIST.TXT, date recorded: Nov. 3, 2020, size: 33 KB).

FIELD

The present disclosure relates to methods of screening (e.g., high-throughput screening) for antagonists of the binding interaction between the receptor sortilin and various sortilin ligands (e.g., progranulin).

BACKGROUND

Sortilin is a Type I transmembrane protein that acts as a receptor of several ligands. In addition, it mediates the sorting of select cargo between the cell surface and the trans-Golgi network (TGN), as well as late endosomes and lysosomes. Sortilin harbors a large extracellular domain that is part of the VPS10 family, homologous to yeast VPS10P. It contains a 10-blade beta-propeller structure and a cysteine-rich 10 CC module (Nykjaer, A. and Willnow, T. E. (2012). *Trends Neurosci.* 35:261-70; Zheng, Y., et al. (2011) *PLoS ONE* 6:e21023).

Sortilin binds directly to multiple ligands, including pro-nerve growth factor (pro-NGF), pro-BDNF, pro-neurotrophin-3, Neurotensin and RAP (Chen, Z. Y., et al. (2005) *J. Neurosci.* 25:6156-66; Mazella, J., et al. (1998) *J. Biol. Chem.* 273:26273-6; Nykjaer, A., et al. (2004) *Nature* 427:843-8; Quistgaard, E. M., et al. (2009) *Nat. Struct. Mol. Biol.* 16:96-8; Yano, H., et al. (2009) *J. Neurosci.* 29:14790-802). Furthermore, Sortilin binds to progranulin (PGRN). This binding leads to rapid endocytosis and lysosomal degradation of PGRN. Sortilin thus negatively regulates the functionally effective levels of extracellular PGRN. In line with this, deficiency of sortilin increases plasma PGRN levels both in mice and humans (Carasquillo, M. M., et al. (2010) *Am. J. Hum. Genet.* 87:890-7; Hu, F., et al. (2010) *Neuron* 68:654-67; Lee, W. C., et al. (2014) *Hum. Mol. Genet.* 23:1467-78).

PGRN binding to sortilin requires its C-terminal most three amino acids (QLL in human, PLL in mouse), and a peptide derived from the last 24 amino acids of PGRN binds with similar affinity as the full-length protein (Zheng, Y., et al. (2011) *PLoS ONE* 6:e21023). It was proposed that this mode of binding is structurally similar to Neurotensin binding (Zheng, Y., et al. (2011) *PLoS ONE* 6:e21023), and there was a successful small molecule screen that identified a blocker of Neurotensin to sortilin binding (Andersen, J. L., et al. (2014) *Acta Crystallogr. D. Biol. Crystallogr.* 70:451-60; Schroder, T. J., et al. (2014) *Bioorg. Med. Chem. Lett.* 24:177-80).

PGRN is a secreted factor that is a risk factor for the development of Frontotemporal Dementia (FTD), accounting for roughly 25% of inherited forms of the disease. Patients with heterozygous loss-of-function mutations in PGRN have >50% reduced extracellular levels of the protein and they will invariably develop FTD, making PGRN a causal gene for the disease (Baker, M., et al. (2006) *Nature* 442:916-9; Carrecchio, M., et al. (2011) *J. Alzheimers Dis.* 27:781-90; Cruts, M. and Van Broeckhoven, C. (2008) *Trends Genet.* 24:186-94; Galimberti, G., et al. (2010) *J. Alzheimers Dis.* 19:171-7). In addition, PGRN mutant alleles have been identified in Alzheimer's (AD) patients (Brouwers, N., et al. (2008) *Neurology* 71:656-64; Sheng, J., et al. (2014) *Gene* 542:141-5) and high levels of extracellular PGRN are protective in models of ALS, Parkinson's disease, Stroke, Arthritis, and Atherosclerosis (Egashira, Y., et al. (2013) *J. Neuroinflammation* 10:105; Laird, A. S., et al. (2010) *PLoS ONE* 5:e13368; Martens, L. H., et al. (2012) *J. Clin. Invest.* 122:3955-9; Tang, W., et al. (2011) *Science* 332:478-84; Tao, J. et al. (2012) *Brain Res.* 1436:130-6; Van Kampen, J. M., et al. (2014) *PLoS ONE* 9:e97032). Sortilin is not considered a functional, signal transducing, receptor for PGRN and cells deficient in sortilin are still responsive to PGRN. The functional PGRN receptor remains to be identified. However, recent studies suggest that PGRN promotes neuronal survival, reduces inflammation and increases A beta endocytosis by microglia (Martens, L. H., et al. (2012) *J. Clin. Invest.* 122:3955-9; Pickford, F., et al. (2011) *Am. J. Pathol.* 178:284-95; Yin, F., et al. (2010) *J. Exp. Med.* 207:117-28).

Accordingly, there is a need for compounds, such as small molecules or proteins (e.g., antibodies), that can increase levels of one or more sortilin ligands (e.g., PGRN) and their associated beneficial effects by blocking the interaction between sortilin and the sortilin ligand(s). Such compounds that inhibit these interactions are potentially highly valuable as treatments for neurodegenerative disorders. For example, increased PGRN may help ameliorate inflammation and neuronal death that occur in FTD and AD. As such, there is a need for screening methods to help identify these compounds.

All references cited herein, including patent applications, patent publications, and UniProtKB/Swiss-Prot Accession numbers are herein incorporated by reference in their entirety, as if each individual reference were specifically and individually indicated to be incorporated by reference.

BRIEF SUMMARY

In order to meet the above needs, the present disclosure provides methods of screening for a sortilin binding antagonist, including: (a) incubating an agent in a solution containing a sortilin protein and a sortilin ligand under conditions in which the sortilin protein is capable of binding to the sortilin ligand, where: (i) a first member of an excitation/emission donor/acceptor pair is attached to the sortilin protein, (ii) a second member of the excitation/emission donor/acceptor pair is attached to the sortilin ligand, and (iii) upon binding between the sortilin protein and the sortilin ligand, the first member and the second member of the fluorescence donor/acceptor pair are in proximity sufficient for proximity-mediated excitation and emission; (b) exciting the excitation/emission donor of the excitation/emission donor/acceptor pair sufficient for proximity-mediated excitation and emission to occur between the excitation/emission donor and the excitation/emission acceptor; and (c) detecting light emitted by the excitation/emission donor at a second wavelength and light emitted by the excitation/emission acceptor at a third wavelength; where a decrease in the ratio of the light emitted by the excitation/emission acceptor at the third wavelength to the light emitted by the excitation/emission donor at the second wavelength, as compared to the ratio in the absence of the agent, indicates that the agent is a sortilin binding antagonist. In some embodiments, the proximity-mediated excitation and emission is fluorescence resonance energy transfer (FRET). In some embodiments, the excitation/emission donor/acceptor pair is a fluorescence donor/acceptor pair, the excitation/emission donor is a fluorescence donor, and the excitation/emission acceptor is a fluorescence acceptor. In some embodiments, the proximity-mediated excitation and emission is bioluminescence resonance energy transfer (BRET). In some embodiments, the excitation/emission donor/acceptor pair is a bioluminescence donor/acceptor pair, the excitation/emission donor is a bioluminescence donor, the excitation/emission acceptor is a bioluminescence acceptor, and the solution further contains a bioluminogenic substrate. In some embodiments, the proximity-mediated excitation and emission is a luminescent oxygen channeling assay (LOCI) or an amplified luminescent proximity homogeneous assay (ALPHA). In some embodiments, the excitation/emission donor/acceptor pair is a singlet oxygen donor/acceptor pair, the excitation/emission donor is a singlet oxygen donor, and the excitation/emission acceptor is a singlet oxygen acceptor.

Certain aspects of the present disclosure relate to methods of screening for a sortilin binding antagonist, including: (a) incubating an agent in a solution containing a sortilin protein and a sortilin ligand under conditions in which the sortilin protein is capable of binding to the sortilin ligand, where: (i) a first member of a fluorescence donor/acceptor pair is attached to the sortilin protein, (ii) a second member of the fluorescence donor/acceptor pair is attached to the sortilin ligand, and (iii) upon binding between the sortilin protein and the sortilin ligand, the first member and the second member of the fluorescence donor/acceptor pair are in proximity sufficient for fluorescence resonance energy transfer (FRET); (b) exciting the fluorescence donor of the fluorescence donor/acceptor pair with light of a first wavelength sufficient for FRET to occur between the fluorescence donor and the fluorescence acceptor; and (c) detecting fluorescence emitted by the fluorescence donor at a second wavelength and fluorescence emitted by the fluorescence acceptor at a third wavelength; where a decrease in the ratio of the fluorescence emitted by the fluorescence acceptor at the third wavelength to the fluorescence emitted by the fluorescence donor at the second wavelength, as compared to the ratio in the absence of the agent, indicates that the agent is a sortilin binding antagonist.

In some embodiments that may be combined with any of the preceding embodiments, the sortilin ligand is a pro-granulin (PGRN) protein. In some embodiments that may be combined with any of the preceding embodiments, the PGRN protein contains the amino acid sequence of SEQ ID NO:3. In some embodiments that may be combined with any of the preceding embodiments, the PGRN protein contains the amino acid sequence of SEQ ID NO:4. In some embodiments that may be combined with any of the preceding embodiments, the sortilin ligand is selected from a neurotensin protein, a pro-sortilin peptide, a spadin peptide, a pro-NGF protein, a PCSK9 protein, or an APP protein. In some embodiments that may be combined with any of the preceding embodiments, the sortilin ligand contains an amino acid sequence selected from SEQ ID NO:5, SEQ ID NO:6, SEQ ID NO:7, SEQ ID NO:8, SEQ ID NO:9, SEQ ID NO:10, and SEQ ID NO:11. In some embodiments that may be combined with any of the preceding embodiments, the sortilin protein contains the amino acid sequence of SEQ ID NO:1. In some embodiments that may be combined with any of the preceding embodiments, the sortilin ligand is coupled to biotin. In some embodiments that may be combined with any of the preceding embodiments, the second member of the fluorescence donor/acceptor pair is coupled to streptavidin, which is attached to the sortilin ligand by binding to the biotin. In some embodiments that may be combined with any of the preceding embodiments, the first member of the fluorescence donor/acceptor pair is coupled to an antibody that specifically binds to the sortilin protein. In some embodiments that may be combined with any of the preceding embodiments, the antibody is a monoclonal antibody. In some embodiments that may be combined with any of the preceding embodiments, the sortilin protein contains a His-tag. In some embodiments that may be combined with any of the preceding embodiments, the first member of the fluorescence donor/acceptor pair is coupled to an antibody that specifically binds to the His-tag. In some embodiments that may be combined with any of the preceding embodiments, the first member of the fluorescence donor/acceptor pair is directly coupled to said sortilin protein. In some embodiments that may be combined with any of the preceding embodiments, the fluorescence donor contains Terbium cryptate. In some embodiments that may be combined with any of the preceding embodiments, the fluorescence acceptor contains XL665. In some embodiments that may be combined with any of the preceding embodiments, the fluorescence acceptor contains d2. In some embodiments that may be combined with any of the preceding embodiments, the first wavelength is about 337 nm. In some embodiments that may be combined with any of the preceding embodiments, the second wavelength is about 620 nm. In some embodiments that may be combined with any of the preceding embodiments, the third wavelength is about 665 nm. In some embodiments that may be combined with any of the preceding embodiments, step (c) occurs after step (b) by a time delay sufficient for decay of short-lived fluorescence. In some embodiments that may be combined with any of the preceding embodiments, the first member of the fluorescence donor/acceptor pair is d2 directly coupled to the sortilin protein, and the second member of the fluorescence donor/acceptor pair contains Terbium cryptate coupled to Streptavidin, which is bound to biotin coupled to the sortilin ligand. In some embodiments that may be combined with any of the preceding embodiments, the first member of the fluorescence donor/acceptor pair is d2 coupled to an antibody that specifically binds to the sortilin protein, and the second member of the fluorescence donor/acceptor pair contains Terbium cryptate coupled to streptavidin, which is bound to biotin coupled to the sortilin ligand. In some embodiments that may be combined with any of the preceding embodiments, the agent is a small molecule or a protein. In some embodiments that may be combined with any of the preceding embodiments, the protein is an antibody that binds to sortilin.

Other aspects of the present disclosure relate to methods of screening for a sortilin binding antagonist, including: (a) contacting a cell expressing a sortilin protein on its cell surface with an agent and a sortilin ligand under conditions in which the sortilin protein is capable of binding to the sortilin ligand, where the sortilin ligand is attached to a fluorophore, and where the fluorophore is associated with the cell upon binding of the sortilin ligand to the sortilin protein; (b) treating the fluorophore associated with the cell with light of a wavelength sufficient to cause the fluorophore to emit fluorescence; and (c) detecting a decrease in the fluorescence emitted by the fluorophore associated with the cell, as compared to the fluorescence emitted by the fluorophore associated with the cell in the absence of the agent, where the decrease in emitted fluorescence indicates that the agent is a sortilin binding antagonist. In some embodiments, the fluorophore is directly coupled to the sortilin ligand. In some embodiments, the sortilin ligand is coupled to biotin, and the fluorophore is coupled to streptavidin, which is attached to the sortilin ligand by binding to the biotin.

Other aspects of the present disclosure relate to methods of screening for a sortilin binding antagonist, including: (a) contacting a cell expressing a sortilin protein on its cell surface with an agent and a sortilin ligand under conditions in which the sortilin protein is capable of binding to the sortilin ligand; and (b) detecting a failure of decrease in the level of the sortilin ligand, as compared to the decrease in the level of the sortilin ligand in the absence of the agent, where the failure of decrease in the level of the sortilin ligand indicates that the agent is a sortilin binding antagonist.

Other aspects of the present disclosure relate to methods of screening for a sortilin binding antagonist, including: (a) culturing a cell that expresses both a sortilin protein on its cell surface and a sortilin ligand in a media under conditions in which the sortilin protein and the sortilin ligand are expressed and the sortilin ligand is released into the media; (b) contacting the cell with an agent under conditions in which the sortilin protein is capable of binding to the sortilin ligand; and (c) detecting an increase in the level of the sortilin ligand in the media, as compared to the level of the sortilin ligand in the media in the absence of the agent, where the increase in the level of the sortilin ligand indicates that the agent is a sortilin binding antagonist.

In some embodiments that may be combined with any of the preceding embodiments, the sortilin ligand is a PGRN protein. In some embodiments that may be combined with any of the preceding embodiments, the PGRN protein contains the amino acid sequence of SEQ ID NO:3. In some embodiments that may be combined with any of the preceding embodiments, the PGRN protein contains the amino acid sequence of SEQ ID NO:4.

It is to be understood that one, some, or all of the properties of the various embodiments described above and herein may be combined to form other embodiments of the present disclosure. These and other aspects of the present disclosure will become apparent to one of skill in the art. These and other embodiments of the present disclosure are further described by the detailed description that follows.

BRIEF DESCRIPTION OF THE DRAWINGS

FIG. 1A) or a sortilin mAb (FIG. 1B) to label to HEK293T cells expressing human sortilin or LacZ (as labeled).

FIGS. 3A-3D show the results of binding assays using four different assay formats (Assay Format 3 in FIG. 3A; Assay Format 5 in FIG. 3B; Assay Format 6 in FIG. 3C; and Assay Format 10 in FIG. 3D). Binding is shown as the HTRF ratio as a function of increasing peptide concentration from 0 to 100 nM sortilin, as labeled.

FIGS. 7A-7C show the specific binding of biotinylated human PGRN to HEK293T cells expressing Sortilin1, but not to control HEK293T cells expressing LacZ. FACS histograms showing binding signal of biotinylated human PGRN are shown in FIG. 7A. Binding curves showing median fluorescence intensity (MFI) as a function of either PGRN or biotinylated PGRN concentration (as labeled) are shown in FIGS. 7B and 7C. Binding curves are provided for both human (FIG. 7B) and mouse (FIG. 7C) PGRN.

FIGS. 10A and 10B show sortilin-mediated PGRN binding and endocytosis using a FACS assay. Median fluorescence intensity (MFI) increased as a function of increasing duration of incubation with 25 nM PGRN-DyLight650. Sortilin-expressing cells were GFP-positive, and untransfected cells were GFP-negative (as labeled in FIG. 10A). PGRN binding and endocytosis were blocked by adding either the C-terminal peptide of PGRN (IC50=35 nM) or the sortilin pro-domain peptide (IC50=450 nM), as shown in FIG. 10B.

DETAILED DESCRIPTION

I. General Techniques

Figure 1A:
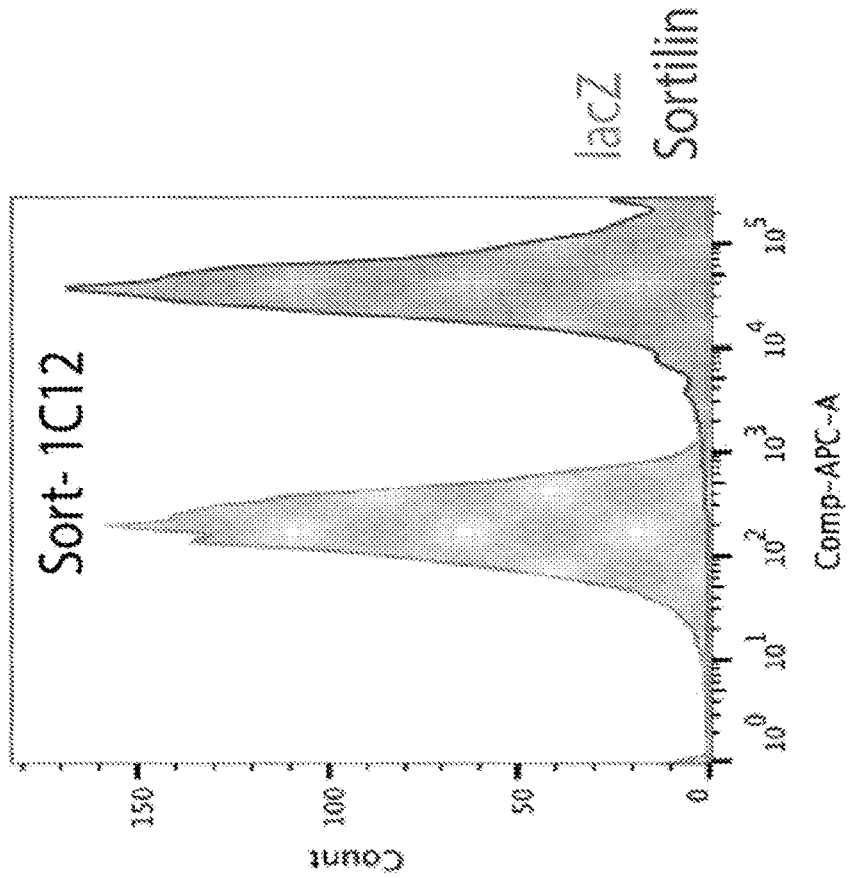
FIGS. 1A and 1B demonstrate the identification of a sortilin-specific monoclonal antibody (1C12, mouse IgG1) that specifically binds to sortilin protein. Shown are FACS histograms depicting the use of a mouse IgG1 control antibody (msIgG1.

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R.I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 1993).

II. Definitions

Before describing the present disclosure in detail, it is to be understood that the present disclosure is not limited to particular compositions or biological systems, which can, of course, vary. It is also to be understood that the terminology used herein is for the purpose of describing particular embodiments only, and is not intended to be limiting.

As used herein and in the appended claims, the singular forms "a," "an," "or," and "the" include plural referents unless the context clearly dictates otherwise.

Reference to "about" a value or parameter herein includes (and describes) variations that are directed to that value or parameter per se. For example, description referring to "about X" includes description of "X".

It is understood that aspects and variations of the present disclosure described herein include "consisting" and/or "consisting essentially of" aspects and variations.

As used herein, an "antagonist" refers to an agent that inhibits interaction between two proteins (e.g., a sortilin protein and a sortilin ligand). The agent may disrupt, reduce, or completely eliminate an interaction between the two proteins. An agent inhibits interaction between two proteins when the agent binds to one of the two proteins.

A "sortilin binding antagonist" may refer to any agent that inhibits interaction between sortilin and one or more sortilin ligands. As used herein, an "interaction" (e.g., an interaction between a sortilin protein and a sortilin ligand) encompasses, without limitation, protein-protein interaction, a physical interaction, a chemical interaction, binding, covalent binding, and ionic binding. As described in greater detail infra, screening for a sortilin binding antagonist is not limited to assaying certain ligands (e.g., progranulin or a sortilin-binding fragment thereof) and may include assaying an interaction between sortilin and any of the sortilin ligands of the present disclosure. In some embodiments, a sortilin binding antagonist that inhibits the interaction between a particular sortilin ligand (e.g., PGRN) and sortilin is specifically identified (e.g., a sortilin-progranulin binding antagonist).

As used herein, a "sortilin ligand" may refer to any molecule (e.g., a polypeptide) that interacts with (e.g., specifically binds) a sortilin protein of the present disclosure. Sortilin ligands may include full-length proteins that bind sortilin as well as any peptide fragments derived therefrom that retain the ability to bind sortilin.

The term "fluorescence resonance energy transfer (FRET)" (also known as Forster resonance energy transfer, resonance energy transfer, and electronic energy transfer) refers to the process by which a donor compound (e.g., a fluorescence donor of the present disclosure) transfers energy to an acceptor compound (e.g., a fluorescence acceptor of the present disclosure) in a non-radiative, non-photon-mediated process that leads to emitted fluorescence. Several FRET-based assays are known in the art, including without limitation time-resolved FRET (TR-FRET), homogeneous time resolved fluorescence (HTRF), and so forth.

A "fluorescence donor/acceptor pair" may refer to any combination of fluorescence donor and fluorescence acceptor compounds that is capable of FRET. When the fluorescence donor emission and the fluorescence acceptor absorption spectra overlap, the donor and acceptor may function as a fluorescence donor/acceptor pair, provided they are within the requisite proximity for FRET to occur. FRET results when excitation energy is transferred from the fluorescence donor to the fluorescence acceptor. Therefore, it will be appreciated by one of skill in the art that, strictly speaking, the fluorescence donor need not donate fluorescence to the fluorescence acceptor per se; rather, the fluorescence donor may simply donate sufficient excitation energy to the fluorescence acceptor such that the fluorescence acceptor emits a photon.

The term "immunoglobulin" (Ig) is used interchangeably with "antibody" herein. The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity, e.g., specific binding to an antigen of interest (such as a sortilin protein of the present disclosure).

The basic 4-chain antibody unit is a heterotetrameric glycoprotein composed of two identical light (L) chains and two identical heavy (H) chains. The pairing of a $V_H$ and $V_L$ together forms a single antigen-binding site. For the structure and properties of the different classes of antibodies, see, e.g., *Basic and Clinical Immunology*, 8th Ed., Daniel P.

Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa ("κ") and lambda ("λ"), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ("α"), delta ("δ"), epsilon ("ε"), gamma ("γ") and mu (μ), respectively. The γ and α classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three dimensional configurations of different classes of immunoglobulins are well known and described generally in, for example, Abbas et al., Cellular and Molecular Immunology, 4$^{th}$ ed. (W. B. Saunders Co., 2000).

The "variable region" or "variable domain" of an antibody refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent-cellular toxicity.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including, for example, the hybridoma method (e.g., Kohler and Milstein, *Nature*, 256:495-97 (1975); Hongo et al., *Hybridoma*, 14 (3):253-260 (1995), Harlow et al., *Antibodies: A Laboratory Manual*, (Cold Spring Harbor Laboratory Press, 2d ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352:624-628 (1991); Marks et al., *J. Mol. Biol.* 222:581-597 (1992); Sidhu et al., *J. Mol. Biol.* 338(2): 299-310 (2004); Lee et al., *J. Mol. Biol.* 340(5):1073-1093 (2004); Fellouse, *Proc. Nat'l Acad. Sci. USA* 101(34):12467-472 (2004); and Lee et al., *J. Immunol. Methods* 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Nat'l Acad. Sci. USA* 90:2551 (1993); Jakobovits et al., *Nature* 362:255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10:779-783 (1992); Lonberg et al., *Nature* 368:856-859 (1994); Morrison, *Nature* 368:812-813 (1994); Fishwild et al., *Nature Biotechnol.* 14:845-851 (1996); Neuberger, *Nature Biotechnol.* 14:826 (1996); and Lonberg and Huszar, *Intern. Rev. Immunol.* 13:65-93 (1995).

As use herein, the term "specifically recognizes" or "specifically binds" refers to measurable and reproducible interactions such as attraction or binding between a target and an antibody, such as an anti-sortilin antibody of the present disclosure, that is determinative of the presence of the target in the presence of a heterogeneous population of molecules including biological molecules. For example, an antibody, such as an anti-sortilin antibody of the present disclosure, that specifically or preferentially binds to a target or an epitope is an antibody that binds this target or epitope with greater affinity, avidity, more readily, and/or with greater duration than it binds to other targets or other epitopes of the target. It is also understood by reading this definition that, for example, an antibody (or a moiety) that specifically or preferentially binds to a first target may or may not specifically or preferentially bind to a second target. As such, "specific binding" or "preferential binding" does not necessarily require (although it can include) exclusive binding. An antibody that specifically binds to a target may have an association constant of at least about $10^3$ M$^{-1}$ or $10^4$ M$^{-1}$, sometimes about $10^5$ M$^{-1}$ or $10^6$ M$^{-1}$, in other instances about $10^6$ M$^{-1}$ or $10^7$ M$^{-1}$, about $10^8$ M$^{-1}$ to $10^9$ M$^{-1}$, or about $10^{11}$ M$^{-1}$ to $10^{11}$M$^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

The terms "polypeptide," "protein," and "peptide" are used interchangeably herein and may refer to polymers of two or more amino acids.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) (e.g., a polynucleotide encoding a sortilin protein of the present disclosure).

A "subject" or an "individual" for purposes of treatment refers to any animal classified as a mammal, including humans, domestic and farm animals, and zoo, sports, or pet animals, such as dogs, horses, cats, cows, etc. Preferably, the mammal is human. The methods described herein may be used, among other uses, to screen for a sortilin binding antagonist of the present disclosure that may be further tested, validated, or modified for use in a subject for the prevention (particularly in an individual at risk) and/or treatment of a disease or disorder, e.g., a neurological disease or disorder such as AD or FTD.

As used herein, the term "preventing" includes providing prophylaxis with respect to occurrence or recurrence of a particular disease, disorder, or condition in an individual. An individual may be predisposed to, susceptible to a particular disease, disorder, or condition, or at risk of developing such a disease, disorder, or condition, but has not yet been diagnosed with the disease, disorder, or condition.

As used herein, an individual "at risk" of developing a particular disease, disorder, or condition may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of a particular disease, disorder, or condition, as known in the art. An individual having one or more of these risk factors has a higher probability of developing a particular disease, disorder, or condition than an individual without one or more of these risk factors.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated", for example, if one or more symptoms associated with a particular disease, disorder, or condition are mitigated or eliminated.

III. FRET-Based Methods

Provided herein are methods of screening for a sortilin binding antagonist. In some embodiments, the methods may include incubating an agent in a solution containing a sortilin protein and a sortilin ligand under conditions in which the sortilin protein is capable of binding to the sortilin ligand. The ability of the agent to disrupt this binding is screened. In some embodiments, a FRET-based method of the present disclosure is used to assay this ability. The methods of screening disclosed herein may be used to assay one or more agents for potential use as a sortilin binding antagonist of the present disclosure. In some embodiments, the methods may involve high-throughput screening (HTS) to screen through numerous agents for said use. The FRET-based methods of the present disclosure are particularly suited for HTS approaches.

Sortilin Proteins

Certain aspects of the present disclosure relate to the use of a sortilin protein. Sortilin is variously referred to as sortilin 1, sort1, 100 kDa NT receptor, glycoprotein 95 (GP95), progranulin receptor (PGRN-R), and neurotensin receptor 3 (NT-3, NTR-3, or NTSR3). Sortilin is an 831 amino acid protein that encodes a type I membrane receptor. Various sortilin homologs are known, including without limitation, human sortilin, rat sortilin, and mouse sortilin. Sortilin proteins of the present disclosure include, without limitation, a mammalian sortilin protein, human sortilin protein, human SorLA protein, human SorCS1 protein, human SorCS2 protein, and human SorCS3 protein.

As used herein, a sortilin protein may refer to a full-length sortilin protein, a processed form of a sortilin protein, a modified form of a sortilin protein (e.g., a sortilin protein comprising a His-tag), or a fragment of a sortilin protein that retains a biological property of interest with the full-length or processed form (e.g., binding to a sortilin ligand, as with an extracellular domain fragment of a sortilin protein).

Sortilin proteins of the present disclosure include several domains, including without limitation, a signal sequence, a propeptide, a luminal domain, a Vps10p domain, a 10 CC domain, a transmembrane domain and a cytoplasmic domain. Additionally, proteins of the present disclosure are expressed at high levels in a number of tissues, including without limitation, the brain, spinal cord, heart and skeletal muscle, thyroid, placenta, and testis.

Sortilin is a member of the Vps10p family of sorting receptors, which also includes, without limitation, sorting protein-related receptor with A-type repeats (SorLA), sortilin-related receptor CNS expressed 1 (SorCS1), sortilin-related receptor CNS expressed 2 (SorCS2), and sortilin-related receptor CNS expressed 3 (SorCS3). The luminal region of sortilin aligns with each of the two luminal domains in yeast Vps10p (Vps10p domains). The hallmark of the Vps10p domain is an amino-terminal propeptide and a carboxy-terminal segment that contains 10 conserved cysteine (10 CC) residues. Other receptors of the Vps10p family share a Vps10p domain, which is situated at the amino-terminus, and contain additional ectodomains.

The Vps10p family of sorting receptors has diverse functions both within the nervous system and elsewhere. The receptors have been shown to be multifunctional, binding several different ligands, including without limitation, pro-granulin, pro-neurotrophins, neurotrophins, pro-neurotrophin-3 (pro-NT3), pro-neurotrophin-4/5, pro-nerve growth factor (Pro-NGF), nerve growth factor (NGF), pro-brain-derived neurotrophic factor (Pro-BDNF), brain-derived neurotrophic factor (BDNF), neurotrophin-3 (NT3), neurotrophin-4/5, neurotensin, p75NTR, sortilin propeptide (Sort-pro), amyloid precursor protein (APP), A beta peptides (A beta), lipoprotein lipase (LpL), apolipoproteins, apolipoprotein AV (APOAS), apolipoprotein E (APOE 2, 3, 4), receptor-associated protein (RAP), and elements of the plasminogen activator system; and engaging in intracellular sorting, endocytosis, and signal transduction. Sortilin proteins of the present disclosure have been shown to mediate rapid endocytosis of lipoprotein lipase, neurotensin, and the pro-form of nerve growth factor; and to target proteins for transport from the Golgi to late endosomes. Further, sortilin proteins of the present disclosure have been shown to form a complex with p75 on the cell membrane and be essential to pro-nerve growth factor (NGF)-induced neuronal death. It has also been recently shown that members of the Vps10p receptor family interact with members of the neurotrophin family, which includes NGF, brain derived neurotrophic factor, neurotrophin-3, and neurotrophin-4/5, or the pro-domain form of a neurotrophin (pro-neurotrophin).

Accordingly, as used herein a "sortilin" protein of the present disclosure includes, without limitation, a mammalian sortilin protein, human sortilin protein, a SorLA protein, a SorCS1 protein, a SorCS2 protein, and a SorCS3 protein.

Additionally, anti-sortilin antibodies of the present disclosure may bind an epitope within one or more of a mammalian sortilin protein, human sortilin protein, a SorLA protein, a SorCS1 protein, a SorCS2 protein, and a SorCS3 protein.

In some embodiments, the sortilin protein is a full-length sortilin protein. In some embodiments, a sortilin protein of the present disclosure comprises the amino acid sequence of SEQ ID NO:2. In some embodiments, a sortilin protein of the present disclosure comprises the amino acid sequence described by the UniProt accession number Q99523.

In some embodiments, the sortilin protein is a mature sortilin extracellular domain. In some embodiments, a sortilin protein of the present disclosure comprises the amino acid sequence of SEQ ID NO:1. In some embodiments, a sortilin protein of the present disclosure comprises the amino acid sequence of SEQ ID NO:1 and a C-terminal His-tag.

Sortilin Ligands

Certain aspects of the present disclosure relate to the use of a sortilin ligand. A sortilin ligand may function as a sortilin ligand in vivo, or it may simply bind to a sortilin protein of the present disclosure in vitro and/or in vivo. Sortilin ligands of the present disclosure may refer to one or more proteins including, without limitation, a progranulin (PGRN) protein or peptide; neurotrophins, such as pro-neurotrophins, pro-neurotrophin-3, neurotrophin-3, pro-neurotrophin-4/5, neurotrophin-4/5, pro-nerve growth factor (pro-NGF), nerve growth factor (NGF), pro-brain-derived neurotrophic factor (Pro-BDNF), and brain-derived neurotrophic factor (BDNF); neurotensin; pro-sortilin, spadin, PCSK9, p75; lipoprotein lipase (LpL); apolipoprotein AV (APOAS); apolipoprotein E (APOE); amyloid precursor protein (APP); A beta peptide; and receptor associated protein (RAP).

In a preferred embodiment, a sortilin ligand of the present disclosure may be a progranulin protein. Sortilin proteins of the present disclosure have been shown to interact (e.g., bind to) directly with progranulin and mediate the degradation of progranulin (e.g., Zheng, Y et al., (2011) PLoS ONE 6(6): e21023). Progranulin is variously referred to as PGRN, proepithelin, granulin-epithelin precursor, PC (prostate cancer) cell-derived growth factor (PCDGF), and acrogranin. Progranulin is a 593 amino acid protein that encodes a 68.5 kDa secreted glycoprotein that has 7.5 repeats of smaller granulin (epithelin) motifs, ranging from 6-25 kDa, which can be proteolytically cleaved from the precursor PGRN. Examples of progranulin cleavage products include, without limitation, granulin A/Epithelins 1, granulin B Epithelins 2, granulin C, granulins D, granulin E, granulin F, granulin G and any other known peptide products derived from pro-granulin.

Progranulin is widely expressed, and in non-neuronal cells has been associated with a variety of events, such as cell cycle regulation and cell motility, wound repair, inflammation, induction of growth factors such as vascular endothelial growth factor (VEGF), and tumorigenesis. Progranulin is also widely expressed in early neural development, but becomes restricted in later development to defined neuronal populations, such as cortical neurons, hippocampal pyramidal neurons, and Purkinje cells. However, the role of progranulin in neuronal cells was unclear until patients suffering from frontotemporal dementia (FTD) were shown to carry mutations in the progranulin gene on chromosome 17. Subsequently, Progranulin has been shown to promote neuronal survival and enhance neurite outgrowth in cortical and motor neurons. Thus, although progranulin is not a neurotrophin, or a member of the neurotrophin family, it has been referred to as a neurotrophic factor because of its ability to promote neuronal survival.

Further, it has been shown that haploinsufficiency of progranulin (which include over 100 different mutations, such as loss-of-function mutations) is associated with frontotemporal dementia (FTD) with TDP-43 pathology. Furthermore, progranulin levels in plasma are reduced with patients with FTD mutations. Progranulin mutations account for 25% of familial FTD. Additionally, low levels of progranulin are seen in some FTD patients without mutations detected. Progranulin has also been reported to be altered in Alzheimer's disease and ALS. Thus, it is believed that progranulin may be generally involved in degenerative diseases.

It has also been shown that complete loss of progranulin leads to a Neuronal Lipoid Fuscinosis (NPL) phenotype. Accordingly, it is believe that individuals with various lysosomal storage disorders may respond to increased levels of progranulin. Progranulin is widely expressed, and in the central nervous system is produced by neurons and microglia. Progranulin is also generally thought to have an anti-inflammatory role in macrophages and microglia, and a pro-survival role in neurons.

Accordingly, a sortilin-progranulin binding antagonist of the present disclosure would be beneficial for preventing, lowering the risk of, or treating conditions and/or diseases associated with decreased levels of progranulin expression and/or activity, cell death (e.g., neuronal cell death), frontotemporal dementia, Alzheimer's disease, vascular dementia, seizures, retinal dystrophy, a traumatic brain injury, a spinal cord injury, long-term depression, atherosclerotic vascular diseases, and/or undesirable symptoms of normal aging.

In some embodiments, a progranulin protein of the present disclosure may include, without limitation, human progranulin, rat progranulin, mouse progranulin, or any other mammalian progranulin. In some embodiments, a progranulin protein of the present disclosure may be a full-length progranulin protein. In some embodiments, a progranulin protein of the present disclosure comprises the amino acid sequence of SEQ ID NO:4.

In some embodiments, a progranulin protein of the present disclosure may include a peptide or fragment of a full-length progranulin protein that retains a biological activity of the full-length protein (e.g., binding a sortilin protein of the present disclosure). It is known that PGRN binding to sortilin requires its C-terminal most three amino acids (QLL in human, PLL in mouse), and a peptide derived from the last 24 amino acids of PGRN binds with similar affinity as the full-length protein (Zheng, Y., et al. (2011) *PLoS ONE* 6:e21023). Without wishing to be bound to theory, it is thought that using a progranulin peptide fragment may increase its stability, and therefore improve the robustness of the methods of the present disclosure. Therefore, in some embodiments, a progranulin protein of the present disclosure comprises the amino acid sequence of SEQ ID NO:3. In some embodiments, a progranulin protein of the present disclosure comprises the amino acid sequence of SEQ ID NO:3 biotinylated at the N-terminus.

While many of the methods disclosed herein employ a progranulin protein as the sortilin ligand, non-progranulin sortilin ligands may also be used. Other sortilin ligands of the present disclosure may interact with a sortilin protein of the present disclosure in a similar mechanism or through a similar binding interface as a progranulin protein and may thus find use in the methods disclosed herein.

In some embodiments, a sortilin ligand is selected from a neurotensin protein, a pro-sortilin peptide, a spadin peptide, a pro-NGF protein, a PCSK9 protein, or an APP protein. In some embodiments, a sortilin ligand may include a neurotensin protein. A neurotensin protein of the present disclosure may refer to a full-length neurotensin protein or a peptide or fragment of a full-length neurotensin protein that retains a biological activity of the full-length protein (e.g., binding a sortilin protein of the present disclosure). In some embodiments, a neurotensin protein may comprise the amino acid sequence described by the UniProt accession number P30990. In some embodiments, a neurotensin protein may comprise the amino acid sequence of SEQ ID NO:5.

In some embodiments, a sortilin ligand may include a pro-sortilin or spadin protein. A pro-sortilin or spadin protein of the present disclosure may refer to a cleavage fragment of full-length sortilin, or derivative thereof, that binds a sortilin protein of the present disclosure). For further description of pro-sortilin and spadin, see, e.g., Munck Petersen, C., et al. (1999) 18:595-604 and Mazella, J., et al. (2010) *PLoS Biol.* 8:e1000355. In some embodiments, a pro-sortilin or spadin protein may comprise the amino acid sequence of SEQ ID NO:6.

In some embodiments, a sortilin ligand may include a nerve growth factor (NGF) protein. An NGF protein of the present disclosure may refer to a full-length NGF protein or a peptide or fragment of a full-length NGF protein that retains a biological activity of the full-length protein (e.g., binding a sortilin protein of the present disclosure). In some embodiments, an NGF protein may comprise the amino acid sequence described by the UniProt accession number P01138. In some embodiments, an NGF protein may comprise the amino acid sequence of SEQ ID NO:7.

In some embodiments, a sortilin ligand may include a proprotein convertase subtilisin/kexin type 9 (PCSK9) protein. A PCSK9 protein of the present disclosure may refer to a full-length PCSK9 protein or a peptide or fragment of a full-length PCSK9 protein that retains a biological activity of the full-length protein (e.g., binding a sortilin protein of the present disclosure). In some embodiments, a PCSK9 protein may comprise the amino acid sequence described by the UniProt accession number Q8NBP7. In some embodiments, a PCSK9 protein may comprise the amino acid sequence of SEQ ID NO:8.

In some embodiments, a sortilin ligand may include an amyloid-beta precursor or amyloid precursor protein (APP). An APP protein of the present disclosure may refer to a full-length APP or amyloid-beta precursor protein, or a peptide or fragment of a full-length APP protein that retains a biological activity of the full-length protein (e.g., binding a sortilin protein of the present disclosure). In some embodiments, a APP protein may comprise the amino acid sequence described by the UniProt accession number P05067. In some embodiments, an APP protein may comprise the amino acid sequence of SEQ ID NO:9. In some embodiments, an APP protein may include a peptide fragment such as A beta peptide (1-40) or A beta peptide (1-42). In some embodiments, an APP protein may comprise the amino acid sequence of SEQ ID NO:10 or SEQ ID NO:11.

Sortilin Binding Antagonists

Certain aspects of the present disclosure relate to methods of screening for a sortilin binding antagonist (e.g., a sortilin-progranulin binding antagonist). The methods of the present disclosure allow for the screening of an agent for potential use as a sortilin binding antagonist of the present disclosure. Several types of agents may be screened using the methods of the present disclosure. In some embodiments, the agent is a small molecule, i.e., their molecular mass is <1,000 Da. In other embodiments, the agent is a protein, e.g., an antibody (such as a full-length antibody, or an antigen-binding fragment thereof) that binds to sortilin. Advantageously, the methods of the present disclosure are robust, sensitive, and reproducible, allowing for HTS approaches useful for testing numerous agents (particularly small molecules).

In some embodiments, the methods of the present disclosure include incubating an agent in a solution containing a sortilin protein and a sortilin ligand under conditions in which the sortilin protein is capable of binding to the sortilin ligand. As used herein, a condition in which a sortilin protein is capable of binding to a sortilin ligand may refer to a parameter or aspect of the environment in which the sortilin protein and sortilin ligand exist (e.g., temperature, pH, a solution, etc.), and conditions may refer to the environment in which the sortilin protein and sortilin ligand exist (e.g., the sum-total of multiple individual conditions). Conditions and solutions in which a sortilin protein is capable of binding to a sortilin ligand are readily known (e.g., the conditions described in the Examples infra) and able to be empirically determined by one of skill in the art using any number of binding assays commonly known in the art (e.g., the assays described in the Examples infra). In some embodiments, such conditions and solutions allow for both the sortilin protein and the sortilin ligand to adopt a natural structure to reproduce the binding interface that would exist between the two partners in vivo. Relevant parameters may include suitable temperature, redox environment, pH, type of solvent (e.g., the amount of DMSO present), and so forth.

Fluorescence Resonance Energy Transfer (FRET)

Certain aspects of the present disclosure relate to the use of FRET to measure a protein-protein interaction (e.g., binding between a sortilin protein and a sortilin ligand). FRET is a concept well-known in the art useful for detecting and/or measuring a distance between two compounds, such as a fluorescence donor/acceptor pair of the present disclosure. When a fluorescence donor is excited by light of a particular wavelength, it may transfer this excitation energy to a fluorescence acceptor through long-range dipole-dipole interaction. Upon excitation, the fluorescence acceptor emits a photon of a longer wavelength than the initial excitation wavelength.

This energy transfer is highly dependent upon the distance between the donor and acceptor—the efficiency of energy transfer is proportional to the inverse sixth power of this distance. This relationship is described by the following equation:

$$E = \frac{1}{1 + (r/R_0)^6}$$

where E is the quantum yield of energy transfer (i.e., FRET efficiency), r is the distance between fluorescence donor and fluorescence acceptor, and $R_0$ is the distance at which energy transfer efficiency is 50% (i.e., the Förster distance or radius).

In some embodiments, the proximity sufficient for FRET is the Förster distance for the fluorescence donor/acceptor pair. The Förster distances for many fluorescence donor/acceptor pairs are known in the art (see, e.g., Sun, Y., et al. (2011) *Chemphyschem*. 12:462-74). In some embodiments, the proximity sufficient for FRET may refer to a distance less than 10 nanometers. In some embodiments, the proximity sufficient for FRET to occur may be between 1 and 10 nanometers.

Additionally, FRET is also dependent upon time. FRET requires that the fluorescence lifetime of the fluorescence donor is longer than the time needed for FRET to occur. The relationship between distance and donor lifetime may be characterized by the following equation:

$$K(t) = (1/\tau_D) \times (R_0/r)^6$$

where K(t) is the energy transfer rate, τD is the donor lifetime in the absence of the fluorescence acceptor, and $R_0$ and r are as described above.

To induce FRET, the fluorescence donor is excited with fluorescence at a wavelength sufficient for FRET to occur. In some embodiments, a wavelength sufficient for FRET to occur between a fluorescence donor and fluorescence acceptor may refer to the range of wavelengths that will excite a fluorescence donor (e.g., a wavelength within the fluorescence donor's absorption spectrum). In some embodiments, the fluorescence donor is excited with a wavelength of light within the fluorescence donor's absorption spectrum but not within the fluorescence acceptor's absorption spectrum to eliminate direct excitation of the fluorescence acceptor independent of FRET. The absorption spectra for a variety of fluorophores are commonly known in the art and available from the fluorophore manufacturer.

To assay FRET signal, fluorescence emitted by the fluorescence acceptor may be detected. In some embodiments, a wavelength detected may refer to the range of wavelengths that are emitted by a fluorescence acceptor (e.g., a wavelength within the fluorescence acceptor's emission spectrum). In some embodiments, the wavelength detected is within the emission spectrum of the fluorescence acceptor, but beyond the emission spectrum of the fluorescence donor, to eliminate detection of non-FRET emissions by the fluorescence donor. The emission spectra for a variety of fluorophores are commonly known in the art and available from the fluorophore manufacturer.

In some embodiments, the proximity-mediated excitation and emission is fluorescence resonance energy transfer (FRET). In some embodiments, the excitation/emission donor/acceptor pair is a fluorescence donor/acceptor pair, the excitation/emission donor is a fluorescence donor, and the excitation/emission acceptor is a fluorescence acceptor. It will also be appreciated by one of skill in the art that proximity-mediated excitation and emission assays other than FRET, e.g., those that do not involve a fluorescence donor may also be used. For example, bioluminescence resonance energy transfer (BRET), in which the donor compound is, e.g., luciferase, may be used in place of FRET. In addition, assays based on the transfer of singlet oxygen are also contemplated. For a description of these assays, see, e.g., the AlphaScreen® or AlphaLISA® systems from Perkin Elmer (Waltham, Mass.) and the luminescent oxygen channeling assay (LOCI) as described in Ullman, E. F. et al. (1994) *Proc. Natl. Acad. Sci.* 91:5426-5430. Therefore, in some embodiments, the proximity-mediated excitation and emission is bioluminescence resonance energy transfer (BRET). In some embodiments, the excitation/emission donor/acceptor pair is a bioluminescence donor/acceptor pair, the excitation/emission donor is a bioluminescence donor (e.g., a luciferase such as *Renilla* luciferase or a derivative thereof), the excitation/emission acceptor is a bioluminescence acceptor (e.g., a fluorescent protein such as GFP or YFP, and derivatives thereof), and the solution further contains a bioluminogenic substrate (e.g., a luciferin such as a coelenterazine or coelenterazine derivative, including without limitation DeepBlueC™). In these embodiments, the bioluminescence donor may be excited by enzymatic activity in the presence of a bioluminogenic substrate, rather than by light. In some embodiments, the proximity-mediated excitation and emission is a luminescent oxygen channeling assay (LOCI) or an amplified luminescent proximity homogeneous assay (ALPHA). In some embodiments, the excitation/emission donor/acceptor pair is a singlet oxygen donor/acceptor pair, the excitation/emission donor is a singlet oxygen donor (e.g., a photosensitizing agent such as phthalocyanine), and the excitation/emission acceptor is a singlet oxygen acceptor (e.g., one or more of thioxene, anthracene, and rubrene). In these embodiments, similar to FRET, the singlet oxygen donor may be excited by light at a wavelength sufficient for singlet oxygen transfer to occur (e.g., about 680 nm).

Fluorescence emitted by the fluorescence donor may also be detected. In some embodiments, the ratio of fluorescence emitted by the fluorescence acceptor to the fluorescence emitted by the fluorescence donor is detected. Upon excitation, fluorescence donors may emit fluorescence not dependent upon FRET. Without wishing to be bound by theory, it is thought that measuring this ratio, instead of only fluorescence emitted by the fluorescence acceptor, may serve as an internal control to correct for signal quenching, variability in the assay medium, and sample-to-sample (e.g., well-to-well) variability (see Degorce, F., et al. (2009) *Current Chemical Genomics* 3:22-32). Additional ways to correct for spectral bleed through between donor and acceptor are described in Sun, Y., et al. (2011) *Chemphyschem.* 12:462-74.

In some embodiments, fluorescence emitted by the fluorescence donor and fluorescence acceptor are detected after a time delay sufficient for decay of short-lived fluorescence following excitation of the fluorescence donor. In some embodiments, a technique such as time-resolved FRET (TR-FRET) or homogeneous time resolved fluorescence (HTRF) may be used. These techniques are based on the principle that non-specific fluorescence emissions typically occur before emissions due to FRET. By incorporating a delay between excitation and detection, the signal from these non-specific emissions may be reduced. For more details, see Degorce, F., et al. (2009) *Current Chemical Genomics* 3:22-32. In some embodiments, a time delay sufficient for decay of short-lived fluorescence may be between 10 and 150 microseconds. In some embodiments, a time delay sufficient for decay of short-lived fluorescence may be between 50 and 150 microseconds. In some embodiments, the time delay sufficient for decay of short-lived fluorescence is less than about any of the following time delays (in microseconds): 150, 140, 130, 120, 110, 100, 90, 80, 70, 60, 50, 40, 30, or 20. In some embodiments, the time delay sufficient for decay of short-lived fluorescence is greater than about any of the following time delays (in microseconds): 10, 20, 30, 40, 50, 60, 70, 80, 90, 100, 110, 120, 130, or 140. That is, the time delay sufficient for decay of short-lived fluorescence can be any of a range of sizes having an upper limit of 150, 140, 130, 120, 110, 100, 90, 80, 70, 60, 50, 40, 30, or 20 and an independently selected lower limit of 10, 20, 30, 40, 50, 60, 70, 80, 90, 100, 110, 120, 130, or 140, wherein the lower limit is less than the upper limit.

Any fluorescence donor known in the art may be used. Preferably, the fluorescence donor forms a suitable fluorescence donor/acceptor pair with the fluorescence acceptor, as described above. In some embodiments, the fluorescence donor is a small molecule or compound. In some embodiments, the fluorescence donor is a fluorescent protein. Exemplary fluorescence donors may be found, inter alia, in Degorce, F., et al. (2009) *Current Chemical Genomics* 3:22-32 or Sun, Y., et al. (2011) *Chemphyschem.* 12:462-74.

In some embodiments, the fluorescence donor comprises Terbium cryptate. In some embodiments, the fluorescence donor comprises Lumi4™-Tb (Cisbio, Codolet, France). In some embodiments, the fluorescence donor comprises Europium cryptate. In some embodiments, the fluorescence donor is excited with a wavelength of about 337 nm. In some embodiments, the fluorescence donor is excited with a wavelength between about 305 nm and about 370 nm. The absorption spectra for various Terbium-based fluorophores are known in the art and commercially available from the manufacturer (e.g., Cisbio).

Any fluorescence acceptor known in the art may be used. Preferably, the fluorescence acceptor forms a suitable fluorescence donor/acceptor pair with the fluorescence donor, as described above. In some embodiments, the fluorescence acceptor is a small molecule or compound. In some embodiments, the fluorescence acceptor is a fluorescent protein. Exemplary fluorescence acceptors may be found, inter alia, in Degorce, F., et al. (2009) *Current Chemical Genomics* 3:22-32 or Sun, Y., et al. (2011) *Chemphyschem.* 12:462-74.

In some embodiments, the fluorescence acceptor comprises XL665. In some embodiments, the fluorescence acceptor comprises d2. In particular, d2 may be used when steric hindrance may present a problem, as the structure of d2 is significantly small than that of XL665. The emission spectra for XL665, d2, and other fluorescence acceptors are known in the art and available from the manufacturer (e.g., Cisbio). In some embodiments, the wavelength emitted by the fluorescence acceptor is detected at about 665 nm. In some embodiments, the wavelength emitted by the fluorescence donor is detected at about 620 nm.

Any suitable method for detecting fluorescence emitted at the appropriate wavelength (e.g., a wavelength described supra) may be used. Fluorescence detection techniques may employ a plate reader (e.g., a PHERAstar plate reader from BMG LABTECH, Ortenberg, Germany), fluorescence microscope, flow cytometer, or any other equipment known in the art for fluorescence detection.

Certain aspects of the present disclosure relate to the use of FRET to assay interaction between a sortilin protein of the present disclosure and a sortilin ligand of the present disclosure. In these assays, one member of a fluorescence donor/acceptor pair may be attached to a sortilin protein, and a cognate member of the fluorescence donor/acceptor pair may be attached to a sortilin ligand. In some embodiments, the fluorescence donor is attached to the sortilin protein, and the fluorescence acceptor is attached to the sortilin ligand. In other embodiments, the fluorescence donor is attached to the sortilin ligand, and the fluorescence acceptor is attached to the sortilin protein.

It will be apparent to one of ordinary skill in the art that these attachments may take various forms. The components may be directly coupled, or they may be indirectly coupled through an intermediary (e.g., antibody binding, biotin:streptavidin binding, an affinity tag, etc.). A member of a fluorescence donor/acceptor pair may be attached at the N-terminus, C-terminus, or any suitable position along the amino acid sequence of the sortilin protein/sortilin ligand. Preferably, the member of the fluorescence donor/acceptor pair is attached such that the folding, stability, and structure of the sortilin protein/sortilin ligand are maintained and the interaction between the sortilin protein/sortilin ligand is not disrupted. Exemplary arrangements and attachments are described and exemplified throughout the present disclosure, but it is to be understood that these examples are in no way intended to be limiting.

In some embodiments, a member of a fluorescence donor/acceptor pair is directly coupled to a sortilin protein of the present disclosure. In some embodiments, the fluorescence donor is directly coupled to a sortilin protein. In other embodiments, the fluorescence acceptor is directly coupled to a sortilin protein. Direct coupling may refer to any method of attachment that lacks an intermediary, such as an antibody, biotin, streptavidin, or an affinity tag. In some embodiments, direct coupling may refer to a direct chemical bond (e.g., a covalent or a non-covalent bond). Methods to couple fluorescence donors or fluorescence acceptors to proteins are known in the art and readily accomplished by commercially available kits (see, e.g., Cisbo d2 labeling kit, Cat. No. 62D2DPEA; Cisbio Europium cryptate labeling kit, Cat. No. 62EUSPEA; Cisbio Terbium cryptate labeling kit, Cat. No. 62TBSPEA; and SNAP-tag® labeling reagents, New England Biolabs and Cisbio).

In some embodiments, a member of a fluorescence donor/acceptor pair is coupled to biotin. Biotin is well known in the art as a way to attach two compounds through its interaction with streptavidin. The biotin:streptavidin bond is specific, quick, and possesses high affinity. Any method known in the art may be used to attach biotin to a member of the fluorescence donor/acceptor pair (i.e., biotinylation), including chemical biotinylation (e.g., through primary amine, carboxyl, sulfhydryl, glycoprotein, or photoactivatable biotinylation) or enzymatic biotinylation (e.g., using biotin, ATP, biotin ligase, and a biotin acceptor peptide).

In some embodiments, a member of a fluorescence donor/acceptor pair is coupled to streptavidin, and the streptavidin is attached to the sortilin ligand/sortilin protein by binding to the biotin. In other embodiments, a member of the fluorescence donor/acceptor pair is coupled to biotin, and the biotin is attached to the sortilin ligand/sortilin protein by binding to the streptavidin. Streptavidin-labeled reagents, e.g., fluorophores, are widely available in the art. For example, streptavidin-labeled fluorescence donors (e.g., comprising Terbium cryptate or Europium) and streptavidin-labeled fluorescence acceptors (e.g., XL665 or d2) are commercially available (Cisbio).

In some embodiments, a member of a fluorescence donor/acceptor pair is coupled to an antibody that specifically binds to a sortilin protein. In other embodiments, a member of a fluorescence donor/acceptor pair is coupled to an antibody that specifically binds to a sortilin ligand. As described infra, antibodies that specifically bind a sortilin protein are known in the art (see, e.g., goat anti-human sortilin antibody AF3154, R&D Systems, Bio-Techne, Minneapolis). Further, as described supra, methods to couple fluorescence donors or fluorescence acceptors to proteins (e.g., an antibody) are known in the art and readily accomplished by commercially available kits (see, e.g., Cisbo d2 labeling kit, Cat. No. 62D2DPEA; Cisbio Europium cryptate labeling kit, Cat. No. 62EUSPEA; Cisbio Terbium cryptate labeling kit, Cat. No. 62TBSPEA; and SNAP-tag® labeling reagents, New England Biolabs and Cisbio).

In some embodiments, the anti-sortilin protein antibody is a monoclonal antibody. As described infra, a variety of technologies to produce monoclonal antibodies are known in the art. Further, as described supra, monoclonal anti-sortilin antibodies have also been used (e.g., antibody 1C12).

In some embodiments, a sortilin protein comprises a His-tag. In some embodiments, a sortilin ligand comprises a His-tag. A His-tag may refer to any polyhistidine motif, such as a motif of six consecutive histidine residues (aka a His6, hexa histidine, or 6×His tag). One of skill in the art will appreciate that any suitable protein tag may be used, such as FLAG, tandem affinity purification (TAP), GST, cMYC, HA, dinitrophenyl (DNP), maltose binding protein (MBP), chitin binding protein (CBP), V5, TEV protease, and the like. Such protein tags may be useful for coupling a motif with a known functionality onto a protein of interest, for example to aid in purification or specific recognition. Typically, a protein tag is placed on the N- or C-terminus of a protein but is not limited to these locations.

In some embodiments, a member of a fluorescence donor/acceptor pair is coupled to an antibody that specifically binds to a His-tag. As such, the anti-His-tag antibody may be used to attach the member of the fluorescence donor/acceptor pair to a sortilin ligand/sortilin protein that comprises a His-tag. Anti-tag antibodies that are coupled to a member of a fluorescence donor/acceptor pair are commercially available (see, e.g., MAb Anti 6HIS-Eu cryptate, Cat. No. 61HISKLA; MAb Anti 6HIS-Tb cryptate, Cat. No. 61HISTLA; MAb Anti 6HIS-XL665, Cat. No. 61HISXLA; and MAb Anti 6HIS-d2, Cat. No. 61HISDLA; all from Cisbio).

Figure 2:
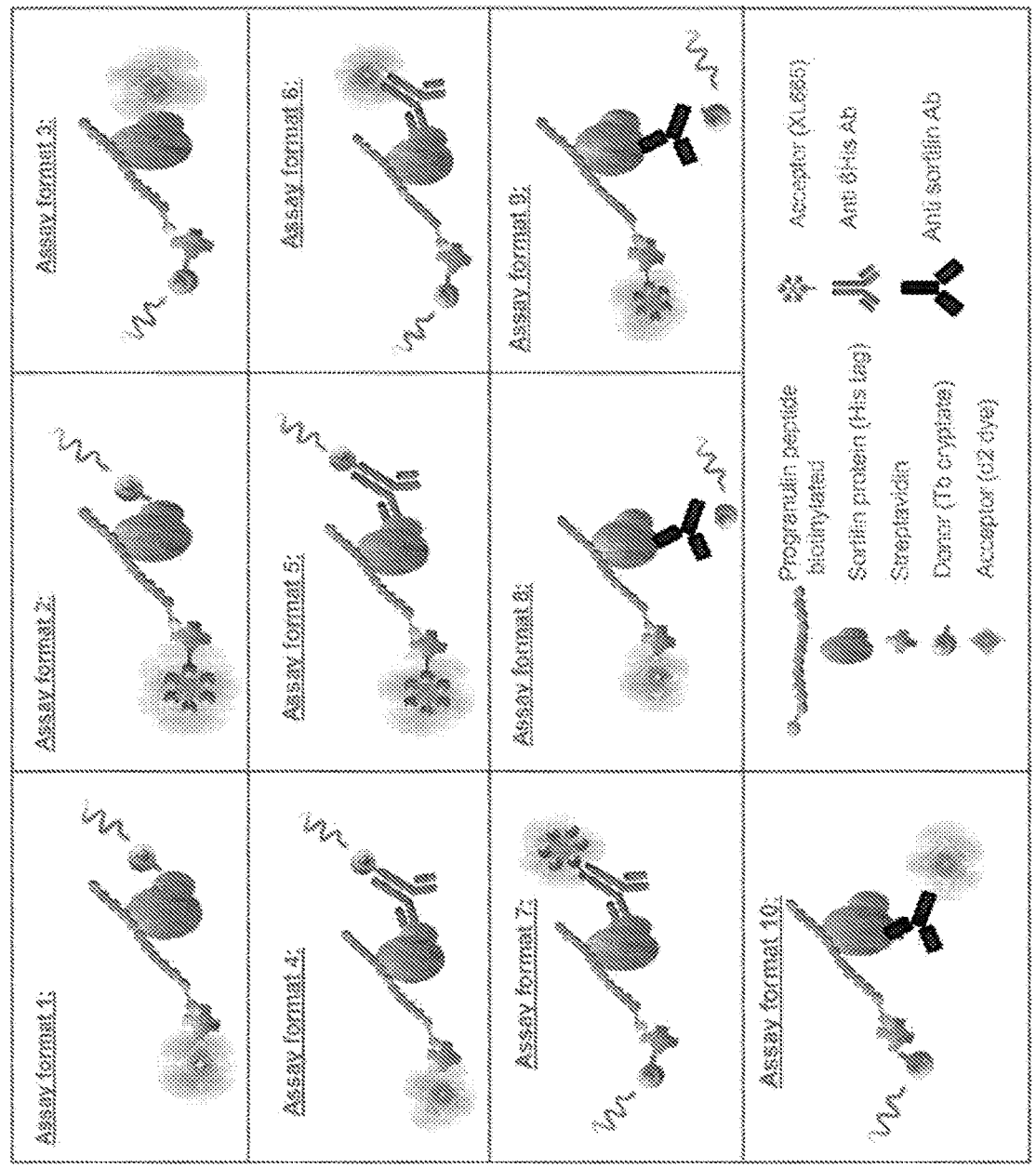
FIG. 2 shows the different assay formats that were used to interrogate binding between sortilin and the PGRN peptide, using Terbium cryptate (Tb) as a donor and d2 or XL665 fluorophores as acceptors (as labeled). For detection, the peptide was bound by streptavidin (SA) coupled donors or acceptors, while sortilin was either directly labeled or bound by an anti-His or anti-sortilin antibody (as labeled).

Numerous embodiments are exemplified and described herein (see, e.g., FIG. 2). In one exemplary and non-limiting embodiment (as illustrated in Assay format 3 in FIG. 2), a sortilin protein is directly coupled to d2 (e.g., a fluorescence acceptor), and a PGRN peptide (e.g., a sortilin ligand) is coupled to biotin, which binds streptavidin coupled to Terbium cryptate (e.g., a fluorescence donor). In another exemplary and non-limiting embodiment (as illustrated in Assay format 10 in FIG. 2), a sortilin protein is bound by an anti-sortilin antibody coupled to d2 (e.g., a fluorescence acceptor), and a PGRN peptide (e.g., a sortilin ligand) is coupled to biotin, which binds streptavidin coupled to Terbium cryptate (e.g., a fluorescence donor). These and other embodiments are described throughout the present disclosure.

In some embodiments of the methods of the present disclosure, false positive compounds that indirectly interfere with any assay readouts of the present disclosure may be discarded. In some embodiments, a counter screen may be designed that utilizes a peptide of the present disclosure (e.g., a sortilin peptide, a sortilin protein, a sortilin ligand, etc.) that is double-labelled. In some embodiments, the peptide may be double-labelled, for example, by biotinylating the N-terminus of the peptide and flag tagging the C-terminus of the peptide. In some embodiments, compounds that interfere with the FRET signal are false positive compounds that may be discarded.

IV. Cell-Based Methods

Further provided herein are methods of screening for a sortilin binding antagonist (e.g., a sortilin-progranulin binding antagonist) that include contacting an agent with a cell expressing a sortilin protein on its cell surface. In some embodiments, the agent and cell are further contacted with a sortilin ligand of the present disclosure (e.g., a PGRN protein of the present disclosure). In some embodiments, the cell itself expresses a sortilin ligand of the present disclosure. These cell-based methods compliment the FRET-based methods described supra, which are amenable to HTS approaches to identify sortilin binding antagonists. The cell-based methods are particularly suited for screening and validating sortilin binding antagonists by assessing the effect on the interaction between sortilin and a sortilin ligand (e.g., a sortilin-PGRN interaction) in the context of a cell.

Certain aspects of the present disclosure relate to a cell expressing a sortilin protein of the present disclosure on its cell surface. In some embodiments, the cell endogenously expresses a sortilin protein of the present disclosure. In some embodiments, the cell is recombinantly engineered to express a sortilin protein of the present disclosure. In any of these embodiments, the sortilin protein of the present disclosure (whether endogenous or recombinant) encoded by the polynucleotide will preferably include at least protein domains required for post-translational processing, membrane translocation, and targeting to the cell surface, including without limitation a signal peptide and a transmembrane domain. In some embodiments, the signal peptide and/or transmembrane domain may refer to the endogenous sortilin signal peptide and/or transmembrane domain. In other embodiments, the signal peptide and/or transmembrane domain may refer to an exogenous signal peptide and/or transmembrane domain known to promote cell surface expression in the desired host cell. In preferred embodiments, the sortilin protein will also contain a domain sufficient for binding a sortilin ligand of the present disclosure (e.g., a PGRN protein of the present disclosure, including without limitation a protein including the amino acid sequences of SEQ ID NO:3 and/or SEQ ID NO:4).

Standard molecular biological techniques well known in the art, such as those described in the references supra, may be used to recombinantly engineer a cell (e.g., a host cell of the present disclosure) to express a sortilin protein of the present disclosure. In some embodiments, the methods include culturing a host cell of the present disclosure containing a polynucleotide encoding the sortilin protein of the present disclosure, under conditions suitable for expression of the antibody.

For recombinant production of a sortilin protein of the present disclosure, a nucleic acid encoding the sortilin protein is isolated and inserted into one or more vectors for further cloning and/or expression in a host cell. Such nucleic acid may be readily isolated and sequenced using conventional procedures (e.g., by using oligonucleotide probes that are capable of binding specifically to a gene encoding the sortilin protein).

Suitable vectors containing a nucleic acid sequence encoding any of the sortilin proteins of the present disclosure, or cell-surface-expressed fragments thereof, described herein include, without limitation, cloning vectors and expression vectors. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a nucleic acid of the present disclosure. The expression vector may replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the nucleic acids of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell. In some embodiments, the vector contains a nucleic acid containing one or more amino acid sequences encoding a sortilin protein of the present disclosure.

Suitable host cells for cloning or expression of antibody-encoding vectors include eukaryotic cells. In preferred embodiments, the host cell of the present disclosure is a mammalian cell, including without limitation monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as Y0, NS0 and Sp2/0. In some embodiments, the host cell is a human cell. In some embodiments, the host cell is a HEK293T cell.

In addition to mammalian cells, eukaryotic microorganisms, such as filamentous fungi or yeast, are also suitable cloning or expression hosts for protein-encoding vectors, including fungi and yeast strains whose glycosylation pathways have been "humanized," resulting in the production of a protein with a partially or fully human glycosylation pattern (e.g., Gerngross, Nat. Biotech. 22:1409-1414 (2004); and Li et al., Nat. Biotech. 24:210-215 (2006)). Suitable host cells for the expression of glycosylated protein can also be derived from multicellular organisms (invertebrates and vertebrates). Examples of invertebrate cells include plant and insect cells (e.g., Sf9 or S2 cells). Numerous baculoviral strains have been identified which may be used in conjunction with insect cells, particularly for transfection of *Spodoptera frugiperda* cells.

In some embodiments, the methods of the present disclosure include contacting a cell expressing a sortilin protein on its cell surface with an agent and a sortilin ligand under conditions in which the sortilin protein is capable of binding to the sortilin ligand. As used herein, a condition in which a sortilin protein is capable of binding to a sortilin ligand may refer to a parameter or aspect of the environment in which the sortilin protein and sortilin ligand exist (e.g., temperature, pH, a solution, etc.), and conditions may refer to the environment in which the sortilin protein and sortilin ligand exist (e.g., the sum-total of multiple individual conditions). These conditions will allow for the sortilin-sortilin ligand interaction to occur, as described above. In preferred embodiments, these methods are also permissive for maintaining cell viability over the timescale of the assay.

In some embodiments, the sortilin ligand is attached to a fluorophore. Any fluorophore known in the art may be used. In some embodiments, the fluorophore may be a fluorescent protein or peptide, including without limitation GFP, RFP, YFP, CFP, derivatives thereof, and the like. In some embodiments, the fluorophore may be a non-protein organic fluorophore, including without limitation a xanthene derivative (e.g., rhodamine, fluorescein, Texas red, etc.), a squaraine derivative, a naphthalene derivative, a cyanine derivative (e.g., cyanine, indocarbocyanine, oxacarbocyanin, etc.), a coumarin derivative, a pyrene derivative, an anthracene derivative, an oxadiazole derivative, an acridine derivative, a tetrapyrrole derivative, an arylmethine derivative, or an oxazine derivative. In some embodiments, the fluorophore may be a quantum dot. Lists of suitable fluorophores and their properties (e.g., absorption and emission spectra, molar extinction coefficient, photobleaching properties, brightness, photostability, and so forth) are commonly obtained through manufacturers, e.g., *The Molecular Probes® Handbook*, 11$^{th}$ ed. (Life Technologies, Carlsbad, Calif.). In some embodiments, the sortilin ligand is attached to a non-fluorescent detection moiety, such as a luminescent or bioluminescent moiety (e.g., a luciferase such as *Renilla* luciferase or a derivative thereof), and a bioluminogenic substrate is further included (e.g., a luciferin such as a coelenterazine or coelenterazine derivative, including without limitation DeepBlueC™).

In some embodiments, the fluorophore attached to the sortilin ligand is associated with the cell upon binding of the sortilin ligand to the sortilin protein. The fluorophore attached to the sortilin ligand may be associated with the cell, for example, if it can be detected on the cell surface and/or detected inside of the cell (e.g., in an endocytic, endosomal, or lysosomal compartment). In this way, detection of emitted fluorescence associated with the cell (e.g., fluorescence on the surface of the cell or inside the cell) allows for detection of an interaction between sortilin and the sortilin ligand in the context of the cell expressing the sortilin. Preferably, the fluorophore itself, and the fluorophore attachment to the sortilin ligand, do not disrupt binding between the sortilin ligand and the sortilin protein expressed by the cell.

In some embodiments, a fluorophore associated with the cell is treated with light of a wavelength sufficient to cause the fluorophore to emit fluorescence. In some embodiments, subsequent fluorescence emitted by the fluorophore associated with the cell is detected. In some embodiments, the wavelength sufficient to cause the fluorophore to emit fluorescence is within the absorption spectrum of the fluorophore. In some embodiments, the wavelength with which the cell is treated is the wavelength of maximum absorption or the excitation maximum. In some embodiments, the wavelength detected is within the emission spectrum of the fluorophore. In some embodiments, the wavelength detected is the emission maximum. As a non-limiting example, DyLight-650 attached to a PGRN protein of the present disclosure may be excited at 652 nm, and emitted fluorescence may be detected at 672 nm. Information on the wavelengths of light sufficient to cause a fluorophore of the present disclosure to emit fluorescence and the wavelengths of light emitted by the fluorophore is widely available in the art and typically supplied by the manufacturer (e.g., Life Technologies, Pierce Biotechnology, Thermo Scientific, abcam, etc.).

Any suitable method for detecting fluorescence emitted at the appropriate wavelength (e.g., a wavelength described supra) may be used. Fluorescence detection techniques may employ a plate reader (e.g., a PHERAstar plate reader from BMG LABTECH, Ortenberg, Germany), fluorescence microscope, flow cytometer, or any other equipment known in the art for fluorescence detection.

In some embodiments, the fluorophore is directly coupled to the sortilin ligand (e.g., a PGRN protein). In some embodiments, the sortilin ligand is coupled to biotin, and the fluorophore is coupled to streptavidin, which is attached to the sortilin ligand by binding to the biotin. Similar to the fluorescence donor/acceptor attachments described supra, the fluorophore may be attached to the sortilin ligand by direct coupling, or they may be indirectly coupled through an intermediary (e.g., antibody binding, biotin:streptavidin binding, an affinity tag, etc.). For example and without limitation, if the fluorophore is a fluorescent protein, the sortilin ligand (e.g., a PGRN protein) may be translated with the coding sequence of the fluorescent protein attached (e.g., by a peptide linker) in-frame with the coding sequence of the sortilin ligand, such that a fusion protein is produced. For example and without limitation, if the fluorophore is a non-protein organic fluorophore, the fluorophore may be chemically attached (e.g., through a covalent bond) to the sortilin ligand. Labeling kits for attaching a fluorophore to a protein of interest (e.g., a PGRN protein of the present disclosure) are commercially available and typically employ a chemical reaction between a primary amine of the protein and an amine-reactive fluorophore or crosslinker. A member of a fluorescence donor/acceptor pair may be attached at the N-terminus, C-terminus, or any suitable position along the amino acid sequence of the sortilin ligand. Typically, a fluorescent protein may be attached to the N- or C-terminus of the sortilin ligand.

In some embodiments, a cell expressing a sortilin protein on its cell surface is contacted with an agent and a sortilin ligand under conditions in which the sortilin protein is capable of binding to the sortilin ligand, the sortilin ligand is attached to a fluorophore, and the fluorophore is associated with the cell upon binding of the sortilin ligand to the sortilin protein. The fluorophore associated with the cell is treated with light of a wavelength sufficient to cause the fluorophore to emit fluorescence; and a decrease in the fluorescence emitted by the fluorophore associated with the cell is detected, as compared to the fluorescence emitted by the fluorophore associated with the cell in the absence of the agent. The decrease in emitted fluorescence indicates that the agent is a sortilin binding antagonist. As shown in the following Examples (see, e.g., FIGS. 9A-9F, 10A, and 10B), and without wishing to be bound to theory, it is thought that an interaction between a sortilin protein of the present disclosure expressed on the surface of a cell and a sortilin ligand (e.g., a PGRN protein) of the present disclosure labeled with a fluorophore of the present disclosure will lead to detectable fluorescence associated with the cell (e.g., on the surface of the cell and/or in the interior of the cell, if the sortilin ligand is internalized by the cell). A sortilin binding antagonist is thought to decrease the fluorescence signal emitted by the fluorophore associated with the cell by reducing this interaction.

In some embodiments, a cell-based assay that operates without emitted fluorescence is used. For example, in some embodiments, a cell expressing a sortilin protein on its cell surface is contacted with an agent and a sortilin ligand under conditions in which the sortilin protein is capable of binding to the sortilin ligand; and a failure of decrease in the level of the sortilin ligand, as compared to the decrease in the level of the sortilin ligand in the absence of the agent, is detected. The failure of decrease in the level of the sortilin ligand (e.g., a PGRN protein) indicates that the agent is a sortilin binding antagonist. As shown in the following Examples (see, e.g., FIG. 11), and without wishing to be bound to theory, it is thought that contacting a sortilin-expressing cell with a sortilin ligand of the present disclosure (e.g., a PGRN protein of the present disclosure) leads to reduction of extracellular sortilin ligand through binding to sortilin, endocytosis, and lysosomal degradation. It is thought that incubating a sortilin-expressing cell with a certain level of the sortilin ligand will lead to a decrease in sortilin ligand over time, and that a sortilin binding antagonist of the present disclosure is able to reduce this decrease (e.g., a failure to decrease). Thus, in comparison with a control treatment, treatment with a sortilin binding antagonist of the present disclosure leads to a failure of decrease in sortilin ligand.

In these embodiments, any cell that expresses a sortilin protein of the present disclosure on its cell surface may be used. In some embodiments, the cell endogenously expresses a sortilin protein of the present disclosure on its cell surface. In some embodiments, the cell is recombinantly engineered to express a sortilin protein of the present disclosure on its cell surface. Any suitable sortilin ligand of the present disclosure may be used (e.g., a PGRN protein), such that it retains the ability to bind to the sortilin protein expressed on the cell surface. The sortilin ligand need not be fluorescently labeled. Levels of sortilin ligand may be detected by any assay known in the art, including without limitation ELISA, Western blotting, mass spectrometry, immunoprecipitation, peptide microarray, and so forth.

In some embodiments, a cell that expresses a sortilin protein of the present disclosure on its cell surface is cultured in a cell culture medium containing a level of a sortilin ligand of the present disclosure. In some embodiments, a known amount of the sortilin ligand is added to the cell culture medium. In some embodiments, a conditioned cell culture medium (e.g., a PGRN-conditioned cell culture medium) may be used, e.g., in which a sortilin ligand of the present disclosure was expressed and secreted into the cell culture medium by a sortilin ligand-producing cell (upon which the sortilin ligand-conditioned cell culture medium is separated from the sortilin ligand-producing cell and subsequently added to the cell that expresses a sortilin protein).

Any suitable cell culture medium useful for culturing a cell that expresses a sortilin protein of the present disclosure on its cell surface may be used. Cell culture media useful for culturing a variety of cell types are known in the art and commercially available. Commercially available media such as Ham's F10 (Sigma), Minimal Essential Medium ((MEM), (Sigma), RPMI-1640 (Sigma), and Dulbecco's Modified Eagle's Medium ((DMEM), Sigma) may be suitable for culturing a cell that expresses a sortilin protein of the present disclosure. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media. Any of these media may be supplemented as necessary with salts (such as sodium chloride, calcium, magnesium, and phosphate), buffers (such as HEPES), growth factors or hormones (such as insulin, transferrin, or epidermal growth factor), nucleotides, antibiotics, trace elements (defined as inorganic compounds usually present at a final concentration in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to one of ordinary skill in the art.

In some embodiments, the methods disclosed herein involve culturing a cell that expresses both a sortilin protein on its cell surface and a sortilin ligand (e.g., a PGRN protein) in a media under conditions in which the sortilin protein and the sortilin ligand are expressed and the sortilin ligand is released into the media; contacting the cell with an agent under conditions in which the sortilin protein is capable of binding to the sortilin ligand; and detecting an increase in the level of the sortilin ligand in the media, as compared to the level of the sortilin ligand in the media in the absence of the agent. An increase in the level of the sortilin ligand indicates that the agent is a sortilin binding antagonist. Without wishing to be bound to theory, it is thought that the interaction between the sortilin protein expressed on the cell surface and the secreted sortilin ligand (e.g., a PGRN protein) will result in endocytosis and lysosomal degradation of the sortilin ligand. Therefore, it is thought that decreasing this interaction (e.g., by addition of a sortilin binding antagonist of the present disclosure) leads to an increase in the level of the sortilin ligand in the media over time.

In these embodiments, any cell that expresses a sortilin protein of the present disclosure on its cell surface and expresses and secretes a sortilin ligand of the present disclosure (e.g., a PGRN protein of the present disclosure) may be used. In some embodiments, the cell may endogenously express a sortilin protein of the present disclosure on its cell surface. In some embodiments, the cell may endogenously express and secrete a sortilin ligand of the present disclosure. In some embodiments, the cell is a U-251 cell, and the sortilin ligand is a PGRN protein. In some embodiments, the cell may be recombinantly engineered to express a sortilin protein of the present disclosure on its cell surface. In some embodiments, the cell may be recombinantly engineered to express and secrete a sortilin ligand of the present disclosure.

In any of the cell-based assays described herein, a sortilin ligand of the present disclosure may be used. In some embodiments, the sortilin ligand is a PGRN protein of the present disclosure. In some embodiments, the PGRN protein comprises the amino acid sequence of SEQ ID NO:3. In some embodiments, the PGRN protein comprises the amino acid sequence of SEQ ID NO:4. The PGRN protein may be a full-length sortilin ligand (e.g., a PGRN protein), or it may be a sortilin-binding peptide fragment thereof.

V. In Silico Methods

Further provided herein are methods of virtually (e.g., in silico) screening for a sortilin binding antagonist (e.g., a sortilin-progranulin binding antagonist).

In some embodiments, a virtual screening method of the present disclosure may be designed to identify novel small molecules (e.g., antagonists) that competitively bind to a progranulin binding site on sortilin. In some embodiments, the C-terminal tail of progranulin (PGRN) may be involved in its interaction with sortilin. In some embodiments, the C-terminal amino acid residues of PGRN may bind similarly to the C-terminal residues of neurotensin. In some embodiments, X-ray structures of sortilin bound both to neurotensin and neurotensin-competitive small molecules may be used as the basis for a combined structure-based and ligand-based virtual screen. In some embodiments, a pool of sortilin binding antagonist compounds may be selected from suitable commercially available libraries.

In some embodiments, a structure-based virtual screening method of the present disclosure includes molecular docking using a program, such as GOLD (Cambridge Crystallographic Data Centre). In some embodiments the crystal structure of sortilin in complex with a small molecule (e.g., AF38469) may be used as a template. In some embodiments, a ligand-based virtual screening approach method of the present disclosure may include use of an X-ray conformation of a small molecule (e.g., AF38469) and a C2-truncated form of neurotensin as input templates for ROCS (OpenEye Scientific Software) and Blaze (Cresset) algorithms.

In some embodiments, a cutoff score may be established using a suitable ligand as a benchmark. In some embodiments, output from the virtual screen may be combined to generate a consensus ranking for one or more candidate sortilin binding antagonists. In some embodiments, the consensus ranking may be combined with an assessment of properties relating to the potential of the one or more candidate sortilin binding antagonists to be successfully developed into oral drugs. In some embodiments, the assessment may include, without limitation, filtering out candidates that contain undesirable or reactive moieties, and filtering out candidates that introduce a bias towards areas of physicochemical property space that have a higher probability of achieving significant CNS penetration, for example as determined using a known CNS multiparameter optimization approach. In some embodiments, the filtered out candidates may be clustered, and one or more representatives may be chosen to cover as wide a range of high scoring chemotypes as possible. In some embodiments, the range of high scoring chemotypes is within a specified limit of 500-1000 candidates.

EXAMPLES

The present disclosure will be more fully understood by reference to the following examples. They should not, however, be construed as limiting the scope of the present disclosure. It is understood that the examples and embodiments described herein are for illustrative purposes only and that various modifications or changes in light thereof will be suggested to persons skilled in the art and are to be included within the spirit and purview of this application and scope of the appended claims.

Example 1: High-Throughput Screening Assays for Sortilin Binding Antagonists

Assays were developed that allow for high-throughput screening to identify sortilin binding antagonists effective in both humans and mice. In order to facilitate high-throughput screening approaches, these assays should be robust, rapid, easy to use, and should accurately recapitulate the interaction between sortilin and a sortilin ligand (e.g., PGRN). As the binding site for sortilin on PGRN can be reproduced by its 24 amino acid-sized C-terminal peptide (Zheng, Y., et al. (2011) *PLoS ONE* 6:e21023), this peptide was employed as a surrogate for PGRN in the screening assays. However, one of skill in the art would readily recognize that the same screen can be conducted with a full-length PGRN protein, such as the mature form of the PGRN protein, or any other sortilin ligand of the present disclosure.

Materials and Methods

Sortilin: PGRN Binding Assays (Assay Formats 1-10)

Biotinylated peptide was used at 1 µM, 100 nM, 10 nM, 1 nM, 0.1 nM, 0.01 nM, 0.001 nM, and 0 nM. The ratio of Streptavidin to Biotin was held constant at 1:4, and SA-Tb (Cisbio, Codolet, France) was used at 0.67 nM. Sortilin protein was tested at 100 nM, 30 nM, 9 nM, 3 nM, 1 nM, 0.24 nM, 0.1 nM and 0 nM. Sortilin was Tb-conjugated by Cisbio. The Tb-conjugated sortilin protein was used at 0.55 nM, 0.21 nM, 0.14 nM, corresponding to 50,000; 25,000; and 12,500 counts at 620 nM. For the anti-6His antibody (Cisbio), the following concentrations were used: anti-6His-d2: 6.67 nM, anti-6His-XL665: 6.67 nM and anti-6His-Tb: 0.7 nM. For the anti-sortilin 1C12 antibody, the following concentrations were used: anti-Sortilin-d2: 6.67 nM, anti-sortilin-Tb: 0.5 nM. All concentrations listed above are final concentrations in a 20 µL assay volume. The reactions took place in phosphate buffered saline (PBS) with 1% BSA.

For the assay runs, the following components were mixed together: 1) 4 µL sortilin protein; 2) 4 µL biotinylated PGRN peptide; 3) 2 µL 10× assay buffer; 4) 5 µL labeled sortilin antibody; and 5) 5 µL SA-Tb. All reagents were incubated for 1 h at room temperature, although the interaction remained stable even after 2 h. The plate was then read on a PHERAstar plate reader (BMG LABTECH, Ortenberg, Germany), with excitation at 337 nm and emission measured after a time-delay at 620 nm and 665 nm. A ratio of 665/620 emission was measured to give relative binding.

For optimization of assay #3, the following concentrations were measured: biotinylated PGRN peptide: 100 nM, 10 nM, 1 nM, 0.1 nM, 0.01 nM, 0.001 nM, 0.0001 nM, 0 nM; sortilin-d2: 30 nM, 9 nM, 3 nM, 1 nM, 0.24 nM and 0 nM; for SA-Tb: 1.3 nM, 0.67 nM and 0.33 nM.

For optimization of assay #10, the following concentrations were measured: biotinylated PGRN peptide: 100 nM, 10 nM, 1 nM, 0.1 nM, 0.01 nM, 0.001 nM, 0.0001 nM, 0 nM; sortilin: 30 nM, 9 nM, 3 nM, 1 nM, 0.24 nM and 0 nM; for SA-Tb: 1.3 nM, 0.67 nM and 0.33 nM.

To discard any false positive compounds that indirectly interfere with the assay readout, a counter screen was designed using double-labeled peptide (N-terminally biotinylated and C-terminally flag tagged). Compounds that interfere with the FRET signal in this assay will be discarded.

Anti-Sortilin Antibody 1C12 Binding Assay

To examine binding of the Sortilin antibody 1C12 to sortilin expressing cells, cells were transiently transfected with human Sortilin or lacZ (control) and GFP using Fugene and harvested after 24 h. Cells were washed in PBS, and 1C12 was added at 5 ug/ml in PBS+2% FBS and incubated on ice for 1 h. After washing cells 3 times in PBS+2% FBS, cells were incubated in anti-mouse-APC secondary antibody (BD Biosciences, 1:20) on ice for 30 min. Then cells were washed again, resuspended in PBS+2% FBS and analyzed on a FACSCanto™ flow cytometer (BD Biosciences, Mississauga, ON). 1C12 binding was analyzed on the GFP positive population.

Sortilin: PGRN Blocking Assays

The above binding assay was tested with the following blocking reagents: non-biotinylated PGRN peptide, sortilin blocking antibody AF3154 (goat polyclonal from R&D Systems, Bio-Techne, Minneapolis), and full-length untagged PGRN protein. For non-biotinylated PGRN peptide, the following concentrations were tested: 1004, 100 nM, 10 nM, 1 nM, 0.1 nM, 0.01 nM and 0 nM. For sortilin blocking antibody, the following concentrations were tested: 1 µM, 100 nM, 10 nM, 1 nM, 0.1 nM, 0.01 nM, 0.001 nM and 0 nM. For full-length untagged PGRN protein, the following concentrations were tested: 1 µM, 100 nM, 10 nM, 1 nM, 0.1 nM, 0.01 nM, 0.001 nM and 0 nM.

DMSO Sensitivity Assays

The above binding assay was tested with the following DMSO concentrations: 10%, 5%, 3%, 1.3%, 0.6%, 0.3%, 0.2%, 0.1%, and 0% (percentages refer to final concentrations). DMSO concentrations were tested using 1 nM or 10 nM biotinylated PGRN peptide.

Cell-Based FACS Assay

HEK293T cells were transiently transfected with constructs for expressing Sortilin or LacZ (control) and incubated with biotinylated PGRN protein on ice for 2 h. Both human and mouse PGRN proteins were tested. Cells were then washed and incubated with Streptavidin-APC and analyzed using Fluorescence Activated Cell Sorting (FACS). For blocking assay, sortilin pro-domain peptide was used. Recombinant human PGRN (Adipogen) was biotinylated using a kit (EZ-link-Micro-NHS-PEG4 biotinylation kit, Thermo Scientific Pierce, #21955). Cells were transiently transfected with human Sortilin or lacZ (control) and GFP using Fugene and harvested after 24 h. GFP was either expressed by a second vector (Topo3.3, Invitrogen) or located on the same vector, separated by an IRES sequence (pCMV6-AC-IRES-GFP, Origene). Full-length Sortilin was used either untagged (Topo3.3) or with a C-terminal myc tag (pCMV6-AC-IRES-GFP). Human Progranulin was added in HBSS+1% BSA or PBS+1% BSA with or without Sortilin pro-peptide as a blocker, and incubated on ice for 2 h. After washing cells 3 times in HBSS+1% BSA, cells were incubated in Streptavidin-APC (BD Biosciences, 1:20) on ice for 30 min. Then cells were washed again, resuspended in HBSS+1% BSA and analyzed on a FACSCanto™ flow cytometer (BD Biosciences, Mississauga, ON). PGRN binding was measured as the median fluorescence intensity of APC on the GFP positive population.

Cell-Based Microscopy Assay

HEK293T cells were transiently transfected with constructs for expressing sortilin or LacZ (control) and incubated with PGRN labeled using DyLight-650 (Life Technologies, Carlsbad, Calif.) for up to 60 minutes at 37° C. Binding and endocytosis of PGRN were observed by fluorescence microscopy. Recombinant human Progranulin (Adipogen) was labeled with DyLight 650 (Life Technologies, Carlsbad, Calif.). Cells were transiently transfected with human Sortilin or lacZ (control) and GFP using Fugene and harvested after 24 h. GFP was either expressed by a second vector (Topo3.3, Invitrogen) or located on the same vector, separated by an IRES (pCMV6-AC-IRES-GFP, Origene). Full-length Sortilin was used either untagged (Topo3.3) or with a C-terminal myc tag (pCMV6-AC-IRES-GFP). Cells were then plated on microscopy chambered glass slides coated with poly-1-lysine. After 4-6 h, cells were washed in OptiMem serum-free media, and 40 nM Progranulin-650 was added with or without 10 uM Sortilin pro-peptide as a blocker. Cells were incubated at 37° C. for up to 60'. Subsequently, cells were fixed in 4% paraformaldehyde, washed in PBS and imaged on a Nikon fluorescent microscope.

Cell-Based PGRN-Conditioned Media Assay

HEK293T cells were transiently transfected with constructs for expressing sortilin or LacZ (control) and incubated with PGRN-conditioned media collected from PGRN transfected HEK293T cells. PGRN levels remaining in the media were measured after 36-48 h using a PGRN ELISA Duoset kit (R&D Systems). Cells were incubated with 1 or 1004 sortilin pro-peptide, 6.7 nM or 67 nM goat anti-sortilin antibody (SORT1 Ab), or 67 nM control IgG.

To prepare hPGRN-conditioned media, Hek293T cells were transiently transfected with full-length, untagged human PGRN (pCMV-Sport6, Thermo Scientific) using Fugene HD (Promega). Media containing PGRN was collected after 48 h. For the experiment, Hek293T cells were transiently transfected with human Sortilin (untagged in Topo3.3) or lacZ (control, Topo3.3) using Fugene HD. After 4-6 h, media containing a 1:5 dilution of PGRN conditioned media was added to the cells with or without blockers [1 or 10 uM Sortilin pro-peptide; 6.7 or 67 nM goat anti-Sortilin antibody (SORT1 Ab, R&D Systems, AF3154) or control IgG (R&D Systems, AB-108-C)]. Cell supernatant was collected after 48 h and analyzed using a PGRN Elisa Duoset kit (R&D Systems, DY2420).

The human U-251 astrocytoid cell line (Sigma), which endogenously expresses Sortilin, was tested for Progranulin secretion with or without blockers. For this experiment, U-251 cells were plated at 12,000 cells/well in a 96 well plate in full media (EMEM) with or without antibodies that block the interaction between Sortilin and Progranulin. 50 nM, 10 nM or 2 nM goat anti-human Sortilin (R&D Systems, AF3154) or 50 nM goat IgG (R&D Systems, AB-108-C) were added to the media. Cells were incubated for 72 h, and the supernatant was collected. Levels of Progranulin secreted by these cells were analyzed using the PGRN Elisa Duoset kit (R&D Systems, DY2420).

Results

The screening assays described herein utilize time-resolved fluorescence that is induced by close proximity between ligand and receptor (e.g., HTRF). Other binding assays such as ELISA, surface plasmon resonance, cell-based binding assays, and cell-based progranulin depletion assays were not sufficiently robust or reproducible to allow high-throughput screening. In contrast, the FRET-based assays described below were the only assays tested that allowed for a high-throughput screening approach to examine large numbers of compounds.

Figure 1B:
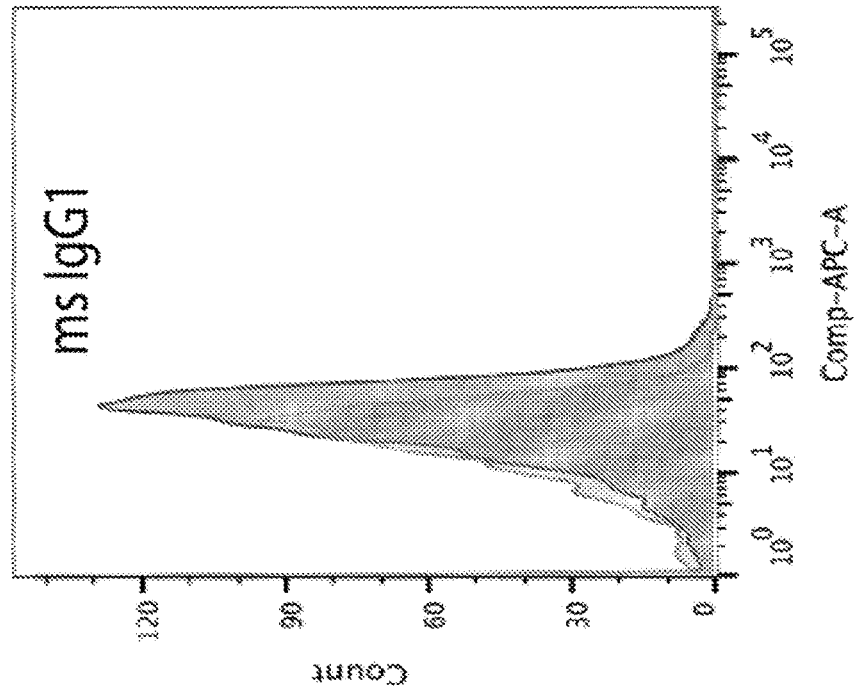

Typically, either the ligand (e.g., a PGRN peptide) or the receptor (e.g., sortilin) was labeled with the fluorescent donor compound Terbium cryptate (Tb), and the other of the ligand/receptor pair was labeled with one of the following fluorescent acceptor molecules: d2 or XL665. The PGRN peptide was synthesized containing an N-terminal Biotin that can be detected by Streptavidin (SA) conjugated to Tb, d2 or XL665. The sortilin protein was engineered to include a C-terminal 6×His-tag. The sortilin protein was detected either by direct conjugation with Tb, d2 or XL665, or by antibody labeling (using an antibody against its His-tag or a monoclonal anti-sortilin antibody 1C12). Both antibodies also can be directly conjugated with Tb, d2 or XL665. As shown in FIGS. 1A and 1B, antibody 1C12 specifically recognizes sortilin, whereas a control IgG1 does not. This property was demonstrated using the cell-based FACS assay described above.

A list of all of the assay format combinations tested is provided in Table 1 below. FIG. 2 further provides a visual depiction of each assay format. The particular concentrations of each component were as described above.

TABLE 1

Assay Formats.

| Peptide† | Protein* | | | | | | |
|---|---|---|---|---|---|---|---|
|  | Direct Tb | Direct d2 | His-Tb | His-d2 | His-XL | Anti-Sort Tb | Anti-Sort d2 |
| SA-Tb |  | Assay #3 |  | Assay #6 | Assay #7 |  | Assay #10 |
| SA-D2 | Assay #1 |  | Assay #4 |  |  | Assay #8 |  |
| SA-XL | Assay #2 |  | Assay #5 |  |  | Assay #9 |  |

*Refers to the sortilin protein.
†Refers to the biotinylated PGRN peptide.

As shown in Table 1 and FIG. 2, ten different assay formats were tested in order to identify assay formats with high sensitivity across a broad assay or signal window. Results from four of the assay formats are depicted in FIG. 3A-3D (assay format numbers 3, 5, 6, and 10 in FIGS. 3A, 3B, 3C, and 3D, respectively). The assays that showed the best performance as measured by sensitivity and assay window size were assay #3 (assay window for 10 nM peptide and 3 nM sortilin ~7.3), assay #6 (assay window ~3.8), and assay #10 (assay window ~5.8).

Figure 4A:
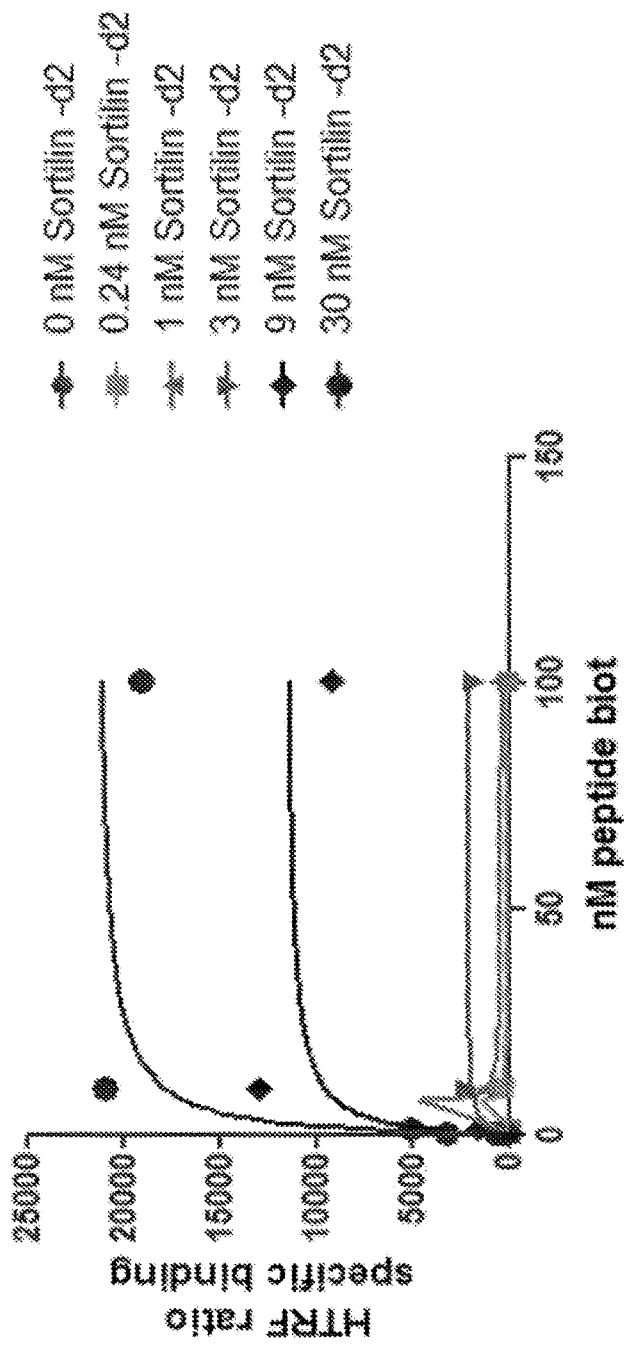
FIGS. 4A and 4B show binding curves for optimized Assay Formats 3 (FIG. 4A) and 10 (FIG. 4B), providing the HTRF ratio as a function of increasing peptide concentration from 0 to 30 nM sortilin, as labeled.
Figure 4B:
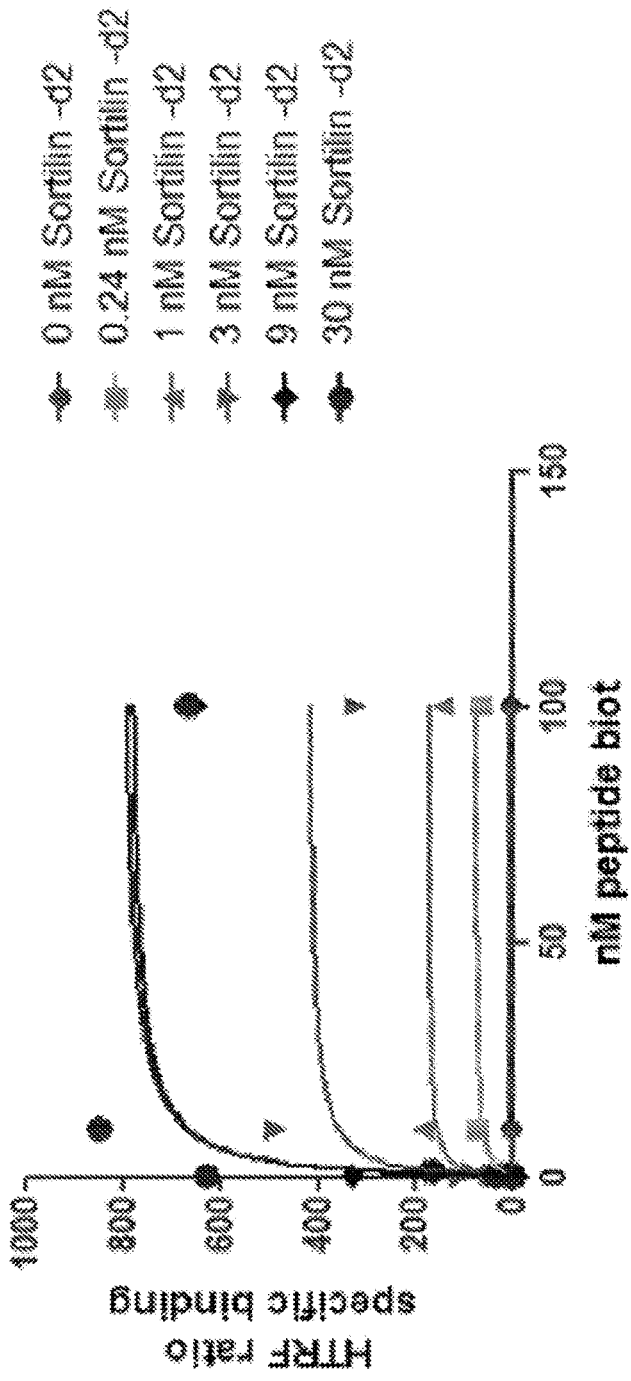

Assays #3 and #10 were then further optimized. Assay #3 uses directly d2 conjugated sortilin and SA-Tb to detect the peptide. Multiple concentrations of biotinylated PGRN peptide were tested as described above. The best format was sortilin-d2 at 9 nM, SA-Tb at 0.33 nM (0.4 ng/well), which measured a binding Kd of 2 nM (FIG. 4A). Assay #10 uses anti-sortilin 1C12 antibody to detect sortilin and SA-Tb to detect the peptide. Multiple concentrations of biotinylated PGRN peptide were tested as described above. The best format was sortilin-d2 at 9 nM, anti-sortilin 1C12 at 20 ng/well, and SA-Tb at 0.33 nM (0.4 ng/well), which measured a binding Kd of 1.6 nM (FIG. 4B).

Figure 5A:
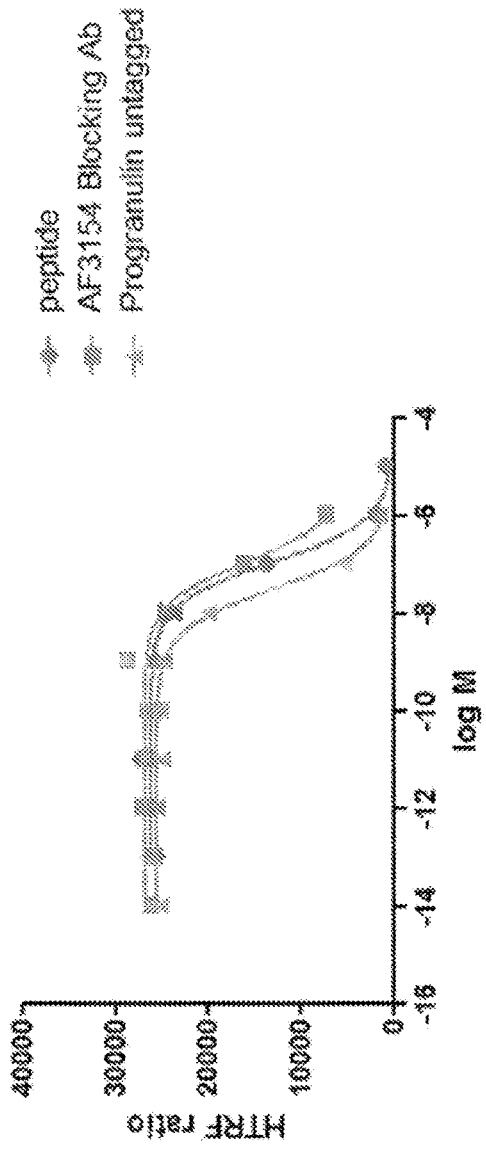
FIGS. 5A and 5B show the results of ligand competition testing for Assay Formats 3 (FIG. 5A) and 10 (FIG. 5B), using 10 nM PGRN peptide and 10 nM sortilin protein. Competition of binding of biotinylated PGRN peptide was tested with unlabeled PGRN peptide, a blocking antibody AF3154, as well as untagged PGRN full-length protein.
Figure 5B:
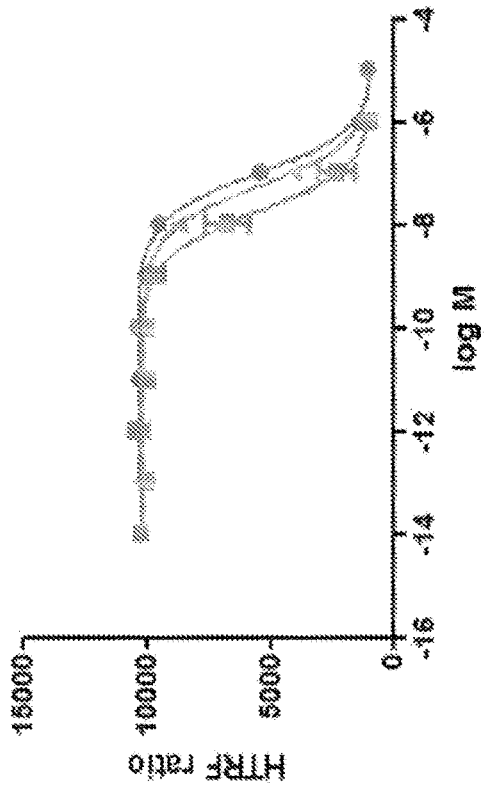

Next, these assay formats were tested for specificity and ability to detect blocking of the sortilin:PGRN interaction. Blocking reagents were employed as described above, using either non-biotinylated PGRN peptide or the anti-sortilin blocking antibody AF3154. Using either assay format #3 or #10, concentration-dependent blocking was observed for all reagents using either 10 nM (assay window=11-26) or 1 nM (assay window=5-9) PGRN peptide. The results of these experiments are shown in FIGS. 5A and 5B for assay format numbers 3 and 10, respectively. Ki's measured were in the mid to low nanomolar range, which is similar to published values.

Figure 6A:
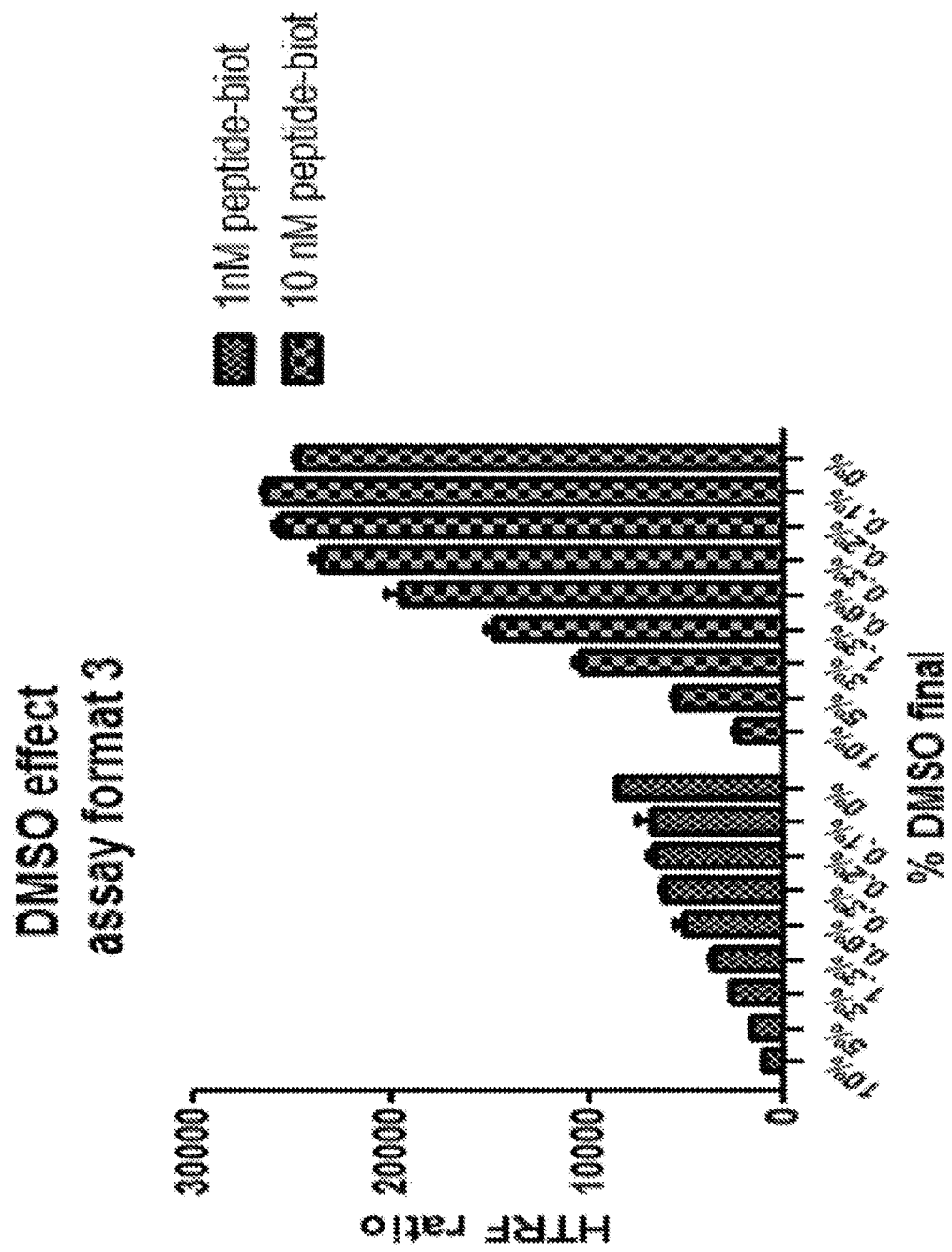
FIGS. 6A and 6B show the effect of increasing DMSO concentration on sortilin: PGRN peptide binding signal for Assay Formats 3 (FIG. 6A) and 10 (FIG. 6B).
Figure 6B:
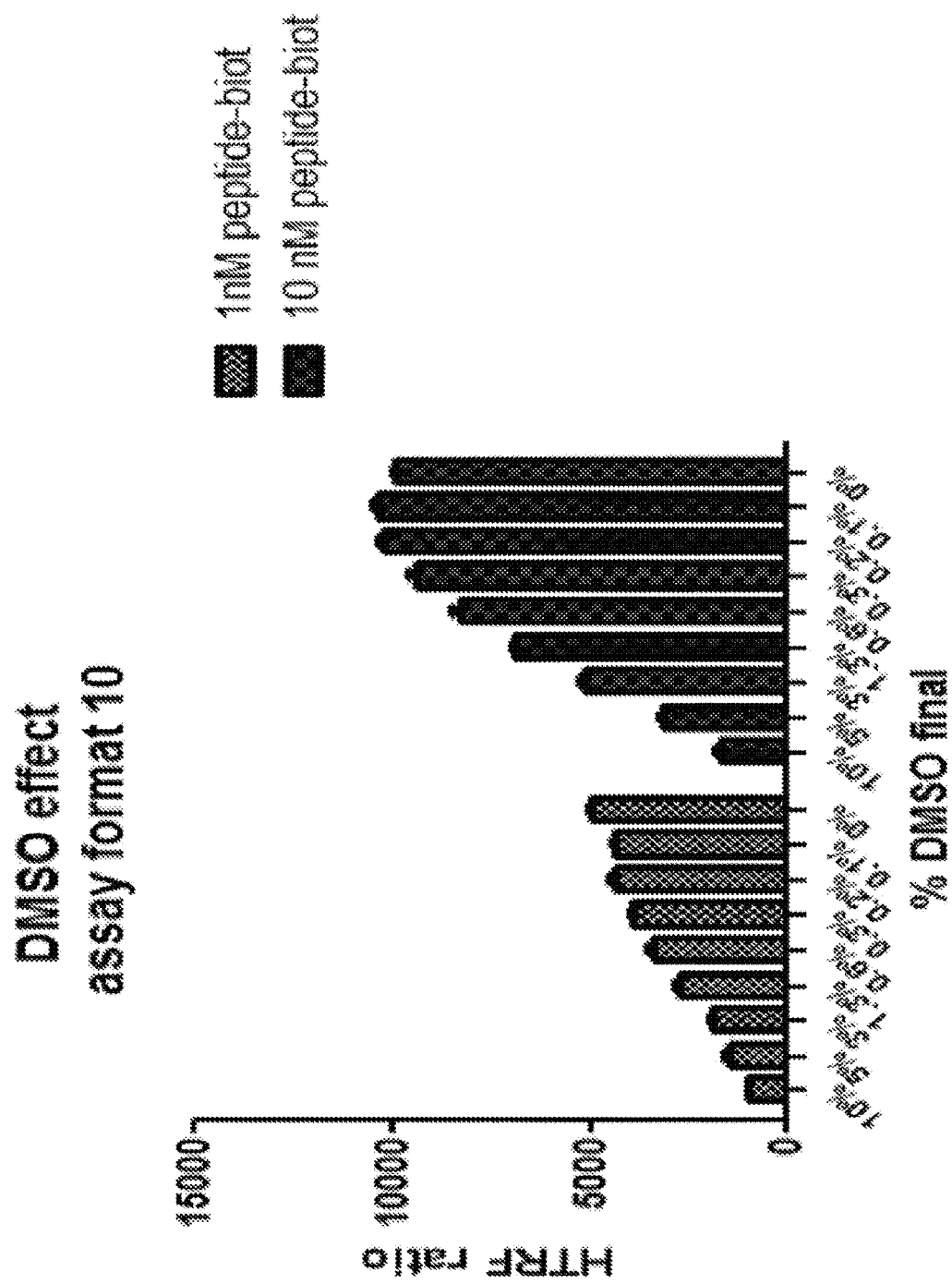

These assay formats were also tested for DMSO sensitivity, since small molecules are often dissolved in DMSO. Both assay formats #3 and #10 tolerated up to 0.3% final concentration of DMSO without a significant drop in signal (FIGS. 6A and 6B, respectively).

Taken together, these experiments demonstrate multiple, sensitive assays amenable to high-throughput screening approaches to identify sortilin binding antagonists. The HTRF-based approaches described above were uniquely robust among a number of alternative binding assays. Among these HTRF-based approaches, certain specific assay formats demonstrated superior performance across multiple parameters, including assay sensitivity, window, specificity, and DMSO tolerance.

Example 2: Cell-Based Assays for Validating Sortilin Binding Antagonists

The previous Example establishes multiple assay formats suitable for high-throughput screening for sortilin binding antagonists. Once such antagonists have been identified, the following cell-based assays may be used to test their functionality in a cellular context.

Figure 8:
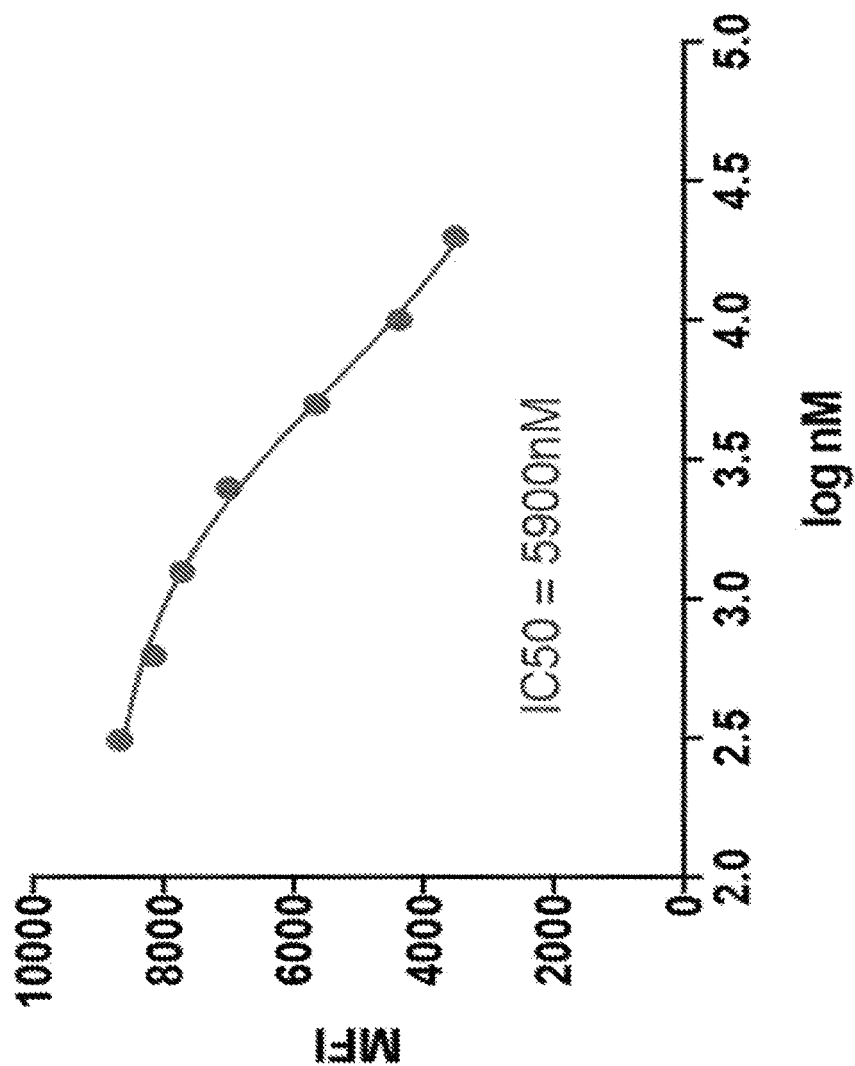
FIG. 8 demonstrates that PGRN binding is blocked by adding a peptide of the Sortilin1 pro-domain, with half maximal blocking at 5.904. Binding curve depicts median fluorescence intensity (MFI) as a function of Sortilin1 pro-domain peptide.

As shown in FIG. 7A, a FACS-based assay was used to demonstrate specific binding of biotinylated human PGRN to HEK293T cells expressing sortilin, but not a control protein (LacZ). This assay revealed strong and specific binding of PGRN to sortilin-expressing, but not control, HEK cells for both human (FIG. 7B) or mouse protein (FIG. 7C), as shown by binding curves generated using the FACS data. Binding was specifically blocked by adding the sortilin pro-domain peptide, with half maximal blocking observed at around 5.9 µM (FIG. 8).

Figures 9A, 9B, 9C, 9D, 9E, 9F:
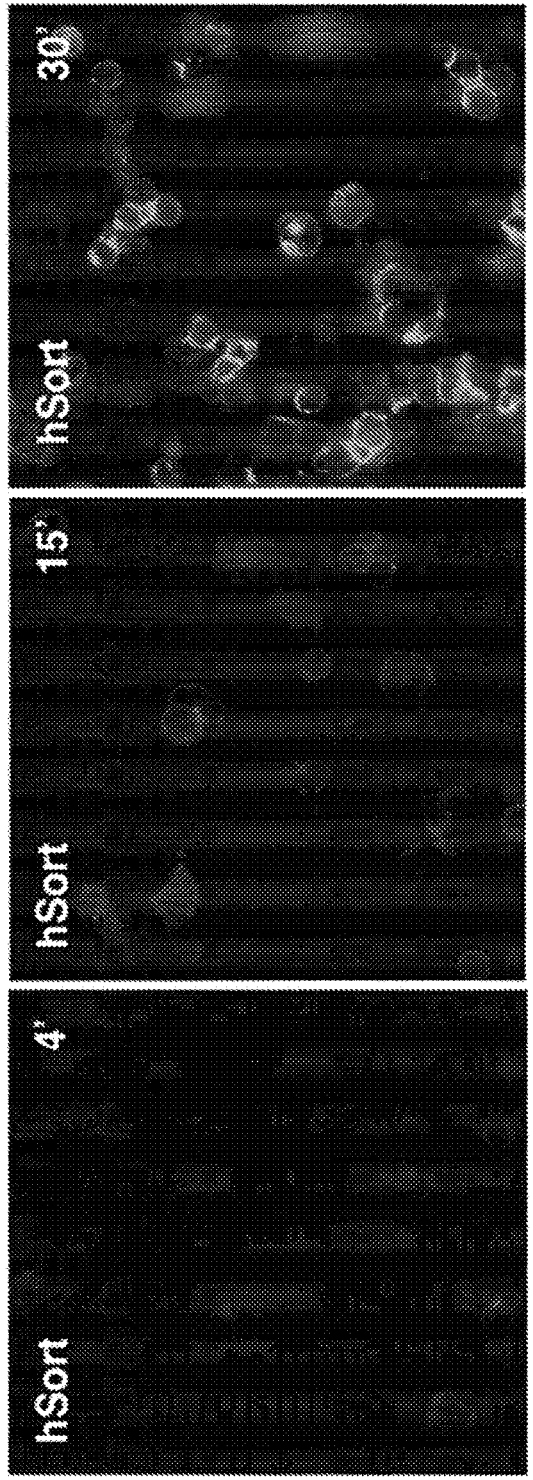
FIGS. 9A-9F show fluorescence microscopic analysis of sortilin-mediated PGRN binding and endocytosis. HEK293T cells were transiently transfected with human sortilin and incubated with DyLight-650 conjugated PGRN (40 nM) for 4 (FIG. 9A), 15 (FIG. 9B), 30 (FIG. 9C), or 60 minutes (FIG. 9D) and showed an increase in PGRN signal over time. In contrast, little signal was observed when using LacZ-expressing cells (control, FIG. 9E) or when 10 μM sortilin pro-peptide was added with the PGRN (FIG. 9F).

A second assay was developed using DyLight-650-conjugated PGRN protein. In this assay, binding and endocytosis of PGRN were observed using either fluorescence microscopy (FIG. 9A-9F) or FACS (FIGS. 10A and 10B). FIG. 9A-9F show that increased binding and endocytosis were observed over time when cells expressed human sortilin, as assayed by DyLight-650 fluorescence (FIG. 9A-9D). However, this was not observed when cells expressed control LacZ protein (FIG. 9E) or were incubated with 10 µM blocking sortilin pro-peptide (FIG. 9F). FIG. 10A shows increased PGRN binding over time to transfected cells, but not control cells, by FACS. FIG. 10B demonstrates that this binding could be blocked by adding either the sortilin pro-peptide or the PGRN C-terminal peptide.

Figure 11:
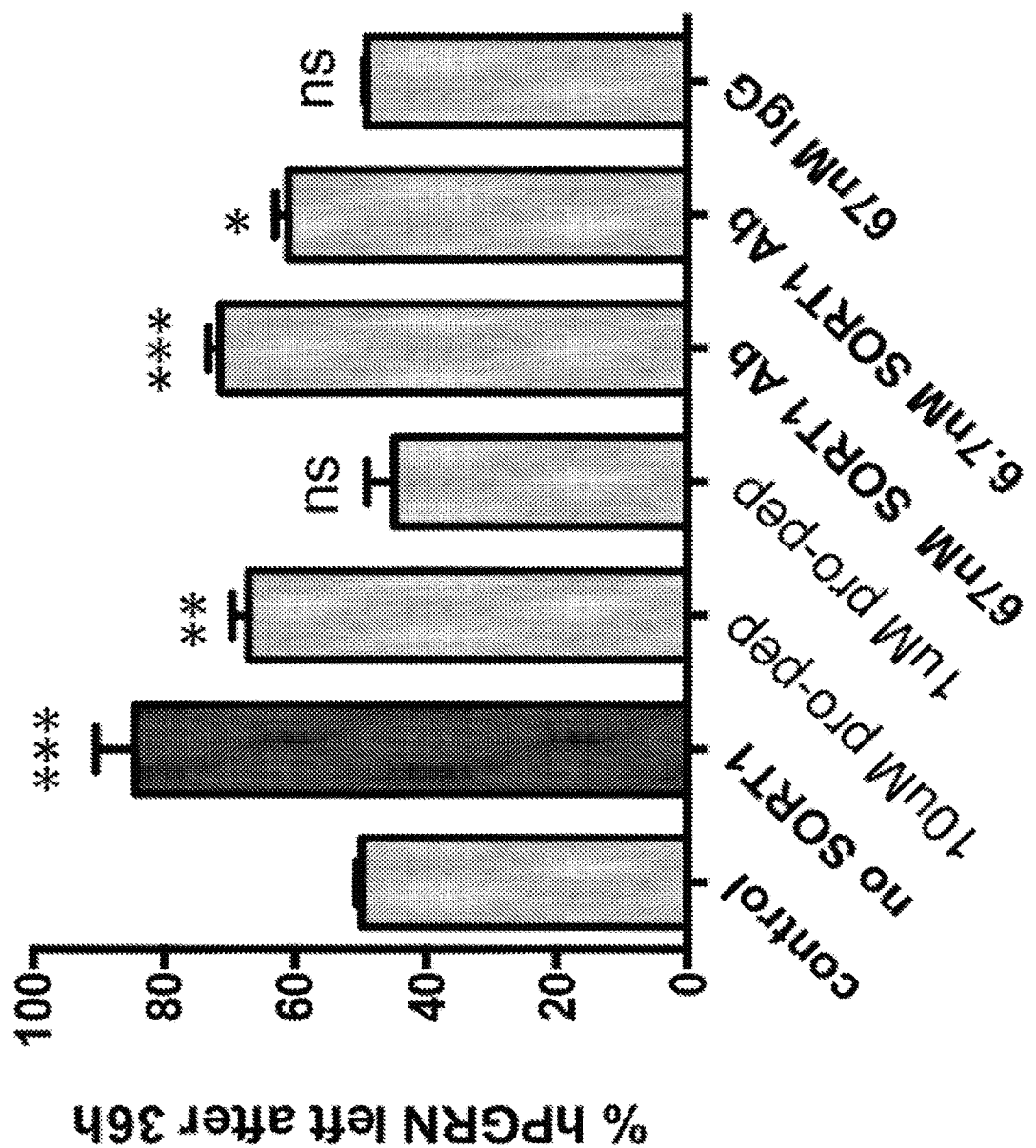
FIG. 11 shows the sortilin-mediated endocytosis and degradation of PGRN in another cell-based assay. Cells were transfected to express human sortilin (light gray) or LacZ (dark gray) and incubated for 36 h in PGRN-conditioned media. The percentage of PGRN remaining was determined by ELISA. Cells were incubated with 1 or 1004 sortilin pro-peptide, 6.7 nM or 67 nM goat anti-sortilin antibody (SORT1 Ab), or 67 nM control IgG, as labeled.

As described above, binding of PGRN to sortilin is known to cause endocytosis, lysosomal targeting and degradation. Thus, sortilin negatively regulates PGRN levels. Another cell-based assay uses the clearance of PGRN from PGRN-conditioned media as a readout for the sortilin:PGRN interaction. In this assay, sortilin-expressing or control HEK293T cells were incubated for 36-48 hours in PGRN-conditioned media, as described above. Expression of sortilin resulted in reduced PGRN levels in the media, which was partially rescued by adding either the sortilin pro-peptide or the goat anti-sortilin AF3154 antibody, but not control IgG (FIG. 11).

Figure 12:
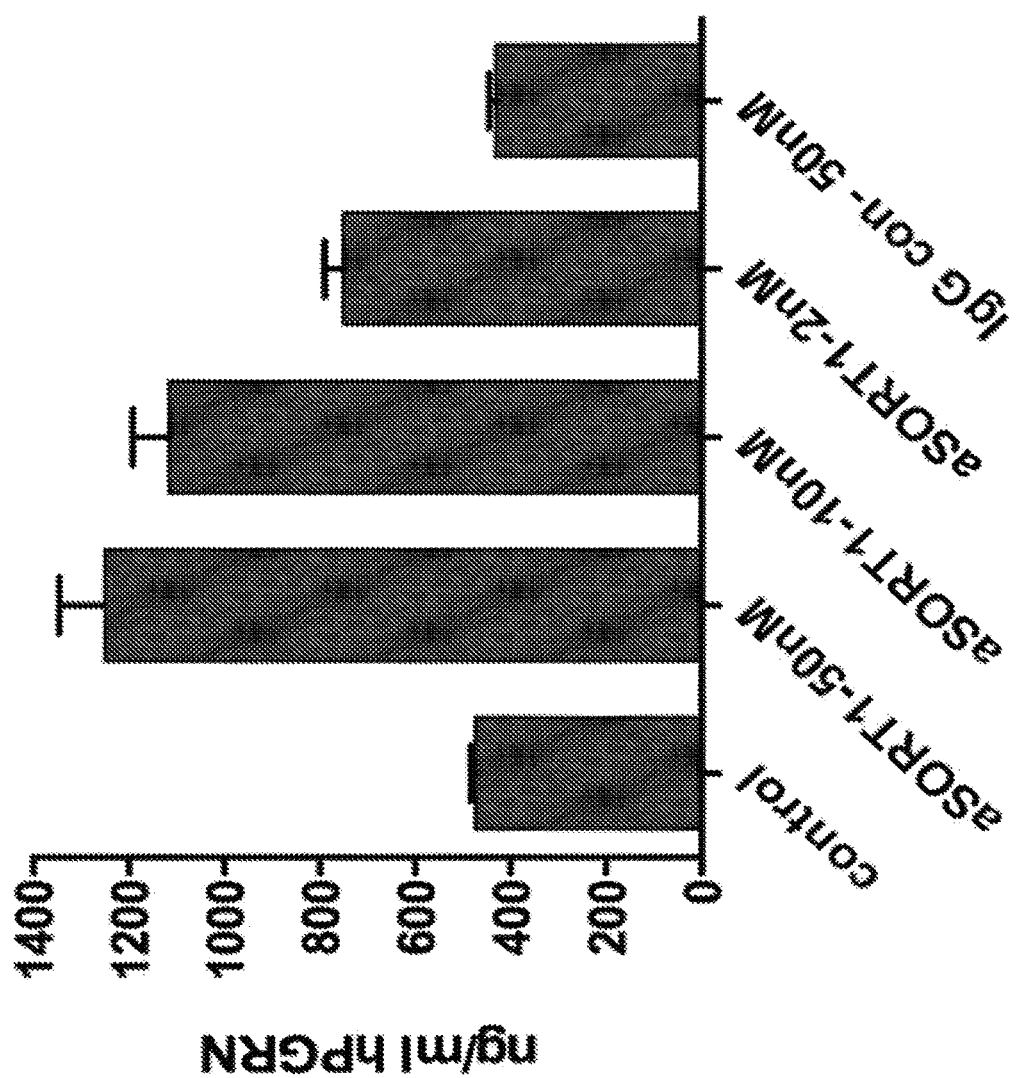
FIG. 12 shows levels of endogenous progranulin secreted by U-251 cells in the absence or presence of antibodies that block binding between progranulin and sortilin (goat anti-sortilin). The presence of blocking antibody prevents endocytosis and degradation of progranulin, thus elevating progranulin levels (detected in the cell supernatant after 72 h).

In a variation on this type of assay, U-251 cells were used. These cells express high endogenous levels of sortilin and also secrete PGRN. U-251 cells were cultured in a cell culture media and incubated with potential sortilin binding antagonists (e.g., anti-human Sortilin antibody), as described above. The level of PGRN secreted into the cell culture media was measured by ELISA after 72 hours (FIG. 12). As shown in FIG. 12, an anti-human Sortilin antibody that acts as a sortilin binding antagonist resulted in a dose-dependent increase in PGRN levels, relative to an agent that did not act as an antagonist (e.g., a control agent, such as an IgG control antibody).

Any small molecule discovered in the high-throughput screening can thus be tested in one or all of these assays for functional blocking of sortilin ligand (e.g., PGRN) binding to sortilin expressed on live cells. Furthermore, these assays will reveal whether such molecules have any effects on cell viability. For example, cell numbers after treatment with small molecules can be measured using a luciferase-based assay (e.g., Cell Titer Glo, Promega). Combined with the high-throughput screening assays described in Example 1, these assays provide a comprehensive platform for identifying and validating potential sortilin binding antagonists.

Example 3: Cell-Based Assays for Validating Sortilin Binding Antagonists

The previous Example describes exemplary assays for testing the ability of small molecules discovered in the high-throughput screening (e.g., as described in Example 1) for functional blocking of sortilin ligand (e.g., PGRN) binding to sortilin expressed on live cells. This Example describes a secondary screen to eliminate small molecules or "hits" from high-throughput screening that non-specifically disrupt FRET signal without blocking the interaction between sortilin and PGRN.

A PGRN peptide (e.g., as described in Example 1) is labeled both on the N-terminus with Biotin and the C-terminus with a FLAG tag. Intramolecular FRET is assayed using a streptavidin-coupled Tb and an anti-FLAG antibody coupled to d2. Molecules that interfere with FRET signal in both a sortilin:Progranulin binding assay (e.g., as described in Example 1) and the intramolecular FRET assay may be considered to non-specifically disrupt FRET signal. Molecules that do not interfere with FRET signal in the intramolecular FRET assay, but do interfere with FRET signal in a sortilin:Progranulin binding assay, are further evaluated (e.g., in a cell-based assay described in Example 2, or another in vivo model system).

Example 4: Virtual Screen to Identify Compounds that Bind Sortilin at the PGRN Binding Site Methods The virtual screening strategy for inhibition of the sortilin-progranulin signaling axis is focused on the identification of novel small molecules that competitively bind to the putative progranulin binding site on sortilin. It is thought that the C-terminal tail of progranulin is critical for its interaction with sortilin, and that these residues bind similarly to the C-terminal residues of neurotensin. As X-ray structures of sortilin bound both to neurotensin and neurotensin-competitive small molecules are available, these will be used as the basis for a combined structure-based and ligand-based virtual screen. The pool of potential compounds will be drawn from a commercial supplier, such as from Asinex, ChemBridge, or Enamine; and will include approximately 3.5 million molecules. In the structure-based virtual screening approach, molecular docking using the program GOLD (Cambridge Crystallographic Data Centre) will be carried out using the crystal structure of sortilin in complex with the small molecule AF38469 (PDB code 4N7E) as a template. In the ligand-based virtual screening approach, the X-ray conformations of AF38469 (PDB code 4N7E) and a C2-truncated form of neurotensin (acyl-I12-L13, PDB code 3F6K) will be used as input templates for the ROCS (OpenEye Scientific Software) and Blaze (Cresset) algorithms.

For each of the virtual screening approaches detailed above, a cutoff score will be established using ligands that have previously been reported as benchmarks. The output from the different methods will then be combined to generate a consensus ranking for the candidate molecules. This virtual screening ranking will then be combined with an assessment of properties relating to the potential of the compounds to be successfully developed into oral drugs. This will include filtering out molecules that contain undesirable or reactive moieties, as well as introducing a bias towards areas of physicochemical property space that have a higher probability of achieving significant CNS penetration, as determined using a published CNS multiparameter optimization approach (ACS Chem Neurosci. 1 (2010) 435-449). Finally, the filtered compound list will be clustered, and representatives chosen to cover as wide a range of high scoring chemotypes as possible within the specified limit of 500-1000 molecules.

What is claimed is:

1. A method of screening for a sortilin binding antagonist, comprising:
   (a) contacting a cell expressing a sortilin protein on its cell surface with an agent and a sortilin ligand under conditions in which the sortilin protein is capable of binding to the sortilin ligand,
   wherein the sortilin ligand is attached to a fluorescent detection donor moiety and wherein the fluorescent detection donor moiety is Terbium cryptate;
      wherein the sortilin protein is attached to a fluorescent detection acceptor moiety and wherein the fluorescent detection acceptor moiety is d2;
   (b) exciting the sortilin ligand attached to Terbium cryptate with light of a first wavelength sufficient for fluorescence resonance energy transfer (FRET) to occur between the Terbium cryptate and the d2; and p1
   (c) detecting fluorescence emitted by the Terbium cryptate at a second wavelength and fluorescence emitted by the d2 at a third wavelength; wherein
      (i) d2 is directly coupled to the sortilin protein, and Terbium cryptate is coupled to Streptavidin, which is bound to biotin coupled to the sortilin ligand; or
      (ii) d2 is coupled to an antibody that specifically binds to the sortilin protein, and Terbium cryptate is coupled to streptavidin, which is bound to biotin coupled to the sortilin ligand; and
   wherein a decrease in the ratio of the fluorescence emitted by the d2 at the third wavelength to the fluorescence emitted by the Terbium cryptate at the second wavelength, as compared to the ratio in the absence of the agent, indicates that the agent is a sortilin binding antagonist.

2. The method of claim 1, wherein said sortilin ligand is a progranulin (PGRN) protein.

3. The method of claim 2, wherein said PGRN protein comprises the amino acid sequence of SEQ ID NO:3.

4. The method of claim 2, wherein said PGRN protein comprises the amino acid sequence of SEQ ID NO:4.

5. The method of claim 1, wherein the sortilin ligand is selected from the group consisting of a neurotensin protein, a pro-sortilin peptide, a spadin peptide, a pro-nerve growth factor (pro-NGF protein), a proprotein convertase subtilisin/kexin type 9 (PCSK9) protein, or an amyloid precursor protein (APP) protein.

6. The method of claim 1, wherein the cell expressing a sortilin protein on its cell surface is a mammalian cell.

7. The method of claim 6, wherein the mammalian cell is selected from the group consisting of a monkey kidney CV1 cell transformed by SV40, a human embryonic kidney cell, a HEK-293 cell, a HEK-293T cell, a baby hamster kidney cell, a mouse sertoli cell, a monkey kidney cell, an African green monkey kidney cell, a human cervical carcinoma cell, a canine kidney cell, a buffalo rat liver cell, a human lung cell, a human liver cell, a mouse mammary tumor cell, a TRI cell, a Chinese hamster ovary cell, and a myeloma cell.

8. The method of claim 6, wherein the mammalian cell is a human embryonic kidney cell.

9. The method of claim 1, wherein the cell expressing a sortilin protein on its cell surface is viable over the timescale of the method.

10. The method of claim 1, wherein the cell expressing a sortilin protein on its cell surface is cultured in a cell culture medium containing the sortilin ligand.

11. The method of claim 1, wherein the agent is a small molecule, wherein the small molecule has molecular mass that is <1,000 Da, or a protein.

12. The method of claim 11, wherein the protein is an antibody that binds to sortilin.

13. The method of claim 1, wherein the failure of decrease in the level of the sortilin ligand is detected by a plate reader, a flow cytometer, or fluorescence microscopy.

14. The method of claim 1, wherein the first wavelength is about 337 nm.

15. The method of claim 1, wherein the second wavelength is about 620 nm.

16. The method of claim 1, wherein the third wavelength is about 665 nm.

* * * * *

SEQUENCE LISTING

<160> NUMBER OF SEQ ID NOS: 11

<210> SEQ ID NO 1
<211> LENGTH: 678
<212> TYPE: PRT
<213> ORGANISM: Homo sapiens

<400> SEQUENCE: 1

```
Ser Ala Pro Gly Glu Asp Glu Glu Cys Gly Arg Val Arg Asp Phe Val
1               5                   10                  15

Ala Lys Leu Ala Asn Asn Thr His Gln His Val Phe Asp Asp Leu Arg
            20                  25                  30

Gly Ser Val Ser Leu Ser Trp Val Gly Asp Ser Thr Gly Val Ile Leu
        35                  40                  45

Val Leu Thr Thr Phe His Val Pro Leu Val Ile Met Thr Phe Gly Gln
    50                  55                  60

Ser Lys Leu Tyr Arg Ser Glu Asp Tyr Gly Lys Asn Phe Lys Asp Ile
65                  70                  75                  80

Thr Asp Leu Ile Asn Asn Thr Phe Ile Arg Thr Glu Phe Gly Met Ala
                85                  90                  95
```

-continued

Ile Gly Pro Glu Asn Ser Gly Lys Val Val Leu Thr Ala Glu Val Ser
            100                 105                 110

Gly Gly Ser Arg Gly Gly Arg Ile Phe Arg Ser Ser Asp Phe Ala Lys
            115                 120                 125

Asn Phe Val Gln Thr Asp Leu Pro Phe His Pro Leu Thr Gln Met Met
            130                 135                 140

Tyr Ser Pro Gln Asn Ser Asp Tyr Leu Leu Ala Leu Ser Thr Glu Asn
145                 150                 155                 160

Gly Leu Trp Val Ser Lys Asn Phe Gly Gly Lys Trp Glu Glu Ile His
                    165                 170                 175

Lys Ala Val Cys Leu Ala Lys Trp Gly Ser Asp Asn Thr Ile Phe Phe
                180                 185                 190

Thr Thr Tyr Ala Asn Gly Ser Cys Lys Ala Asp Leu Gly Ala Leu Glu
            195                 200                 205

Leu Trp Arg Thr Ser Asp Leu Gly Lys Ser Phe Lys Thr Ile Gly Val
            210                 215                 220

Lys Ile Tyr Ser Phe Gly Leu Gly Gly Arg Phe Leu Phe Ala Ser Val
225                 230                 235                 240

Met Ala Asp Lys Asp Thr Thr Arg Arg Ile His Val Ser Thr Asp Gln
                245                 250                 255

Gly Asp Thr Trp Ser Met Ala Gln Leu Pro Ser Val Gly Gln Glu Gln
                260                 265                 270

Phe Tyr Ser Ile Leu Ala Ala Asn Asp Asp Met Val Phe Met His Val
            275                 280                 285

Asp Glu Pro Gly Asp Thr Gly Phe Gly Thr Ile Phe Thr Ser Asp Asp
            290                 295                 300

Arg Gly Ile Val Tyr Ser Lys Ser Leu Asp Arg His Leu Tyr Thr Thr
305                 310                 315                 320

Thr Gly Gly Glu Thr Asp Phe Thr Asn Val Thr Ser Leu Arg Gly Val
                325                 330                 335

Tyr Ile Thr Ser Val Leu Ser Glu Asp Asn Ser Ile Gln Thr Met Ile
                340                 345                 350

Thr Phe Asp Gln Gly Gly Arg Trp Thr His Leu Arg Lys Pro Glu Asn
            355                 360                 365

Ser Glu Cys Asp Ala Thr Ala Lys Asn Lys Asn Glu Cys Ser Leu His
            370                 375                 380

Ile His Ala Ser Tyr Ser Ile Ser Gln Lys Leu Asn Val Pro Met Ala
385                 390                 395                 400

Pro Leu Ser Glu Pro Asn Ala Val Gly Ile Val Ile Ala His Gly Ser
                405                 410                 415

Val Gly Asp Ala Ile Ser Val Met Val Pro Asp Val Tyr Ile Ser Asp
                420                 425                 430

Asp Gly Gly Tyr Ser Trp Thr Lys Met Leu Glu Gly Pro His Tyr Tyr
            435                 440                 445

Thr Ile Leu Asp Ser Gly Gly Ile Ile Val Ala Ile Glu His Ser Ser
            450                 455                 460

Arg Pro Ile Asn Val Ile Lys Phe Ser Thr Asp Glu Gly Gln Cys Trp
465                 470                 475                 480

Gln Thr Tyr Thr Phe Thr Arg Asp Pro Ile Tyr Phe Thr Gly Leu Ala
                485                 490                 495

Ser Glu Pro Gly Ala Arg Ser Met Asn Ile Ser Ile Trp Gly Phe Thr
            500                 505                 510

Glu Ser Phe Leu Thr Ser Gln Trp Val Ser Tyr Thr Ile Asp Phe Lys

```
            515                 520                 525
Asp Ile Leu Glu Arg Asn Cys Glu Glu Lys Asp Tyr Thr Ile Trp Leu
            530                 535                 540

Ala His Ser Thr Asp Pro Glu Asp Tyr Glu Asp Gly Cys Ile Leu Gly
545                 550                 555                 560

Tyr Lys Glu Gln Phe Leu Arg Leu Arg Lys Ser Ser Val Cys Gln Asn
                    565                 570                 575

Gly Arg Asp Tyr Val Val Thr Lys Gln Pro Ser Ile Cys Leu Cys Ser
                580                 585                 590

Leu Glu Asp Phe Leu Cys Asp Phe Gly Tyr Tyr Arg Pro Glu Asn Asp
                595                 600                 605

Ser Lys Cys Val Glu Gln Pro Glu Leu Lys Gly His Asp Leu Glu Phe
            610                 615                 620

Cys Leu Tyr Gly Arg Glu Glu His Leu Thr Thr Asn Gly Tyr Arg Lys
625                 630                 635                 640

Ile Pro Gly Asp Lys Cys Gln Gly Gly Val Asn Pro Val Arg Glu Val
                    645                 650                 655

Lys Asp Leu Lys Lys Lys Cys Thr Ser Asn Phe Leu Ser Pro Glu Lys
                660                 665                 670

Gln Asn Ser Lys Ser Asn
                675

<210> SEQ ID NO 2
<211> LENGTH: 831
<212> TYPE: PRT
<213> ORGANISM: Homo sapiens

<400> SEQUENCE: 2

Met Glu Arg Pro Trp Gly Ala Ala Asp Gly Leu Ser Arg Trp Pro His
1               5                   10                  15

Gly Leu Gly Leu Leu Leu Leu Gln Leu Leu Pro Pro Ser Thr Leu
            20                  25                  30

Ser Gln Asp Arg Leu Asp Ala Pro Pro Pro Ala Ala Pro Leu Pro
        35                  40                  45

Arg Trp Ser Gly Pro Ile Gly Val Ser Trp Gly Leu Arg Ala Ala Ala
50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
                100                 105                 110

Ser Leu Ser Trp Val Gly Asp Ser Thr Gly Val Ile Leu Val Leu Thr
            115                 120                 125

Thr Phe His Val Pro Leu Val Ile Met Thr Phe Gly Gln Ser Lys Leu
130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
                180                 185                 190

Arg Gly Gly Arg Ile Phe Arg Ser Ser Asp Phe Ala Lys Asn Phe Val
            195                 200                 205
```

-continued

```
Gln Thr Asp Leu Pro Phe His Pro Leu Thr Gln Met Met Tyr Ser Pro
    210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Phe Thr Thr Tyr
                260                 265                 270

Ala Asn Gly Ser Cys Lys Ala Asp Leu Gly Ala Leu Glu Leu Trp Arg
                275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
                340                 345                 350

Ile Leu Ala Ala Asn Asp Asp Met Val Phe Met His Val Asp Glu Pro
                355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
                420                 425                 430

Gln Gly Gly Arg Trp Thr His Leu Arg Lys Pro Glu Asn Ser Glu Cys
                435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
                500                 505                 510

Tyr Ser Trp Thr Lys Met Leu Glu Gly Pro His Tyr Tyr Thr Ile Leu
    515                 520                 525

Asp Ser Gly Gly Ile Ile Val Ala Ile Glu His Ser Ser Arg Pro Ile
530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
                580                 585                 590

Leu Thr Ser Gln Trp Val Ser Tyr Thr Ile Asp Phe Lys Asp Ile Leu
                595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
```

```
                625                 630                 635                 640
    Gln Phe Leu Arg Leu Arg Lys Ser Ser Val Cys Gln Asn Gly Arg Asp
                    645                 650                 655

Tyr Val Val Thr Lys Gln Pro Ser Ile Cys Leu Cys Ser Leu Glu Asp
                    660                 665                 670

Phe Leu Cys Asp Phe Gly Tyr Tyr Arg Pro Glu Asn Asp Ser Lys Cys
                    675                 680                 685

Val Glu Gln Pro Glu Leu Lys Gly His Asp Leu Glu Phe Cys Leu Tyr
                    690                 695                 700

Gly Arg Glu Glu His Leu Thr Thr Asn Gly Tyr Arg Lys Ile Pro Gly
    705                 710                 715                 720

Asp Lys Cys Gln Gly Gly Val Asn Pro Val Arg Glu Val Lys Asp Leu
                    725                 730                 735

Lys Lys Lys Cys Thr Ser Asn Phe Leu Ser Pro Glu Lys Gln Asn Ser
                    740                 745                 750

Lys Ser Asn Ser Val Pro Ile Ile Leu Ala Ile Val Gly Leu Met Leu
                    755                 760                 765

Val Thr Val Val Ala Gly Val Leu Ile Val Lys Lys Tyr Val Cys Gly
                    770                 775                 780

Gly Arg Phe Leu Val His Arg Tyr Ser Val Leu Gln Gln His Ala Glu
    785                 790                 795                 800

Ala Asn Gly Val Asp Gly Val Asp Ala Leu Asp Thr Ala Ser His Thr
                    805                 810                 815

Asn Lys Ser Gly Tyr His Asp Asp Ser Asp Glu Asp Leu Leu Glu
                    820                 825                 830

<210> SEQ ID NO 3
<211> LENGTH: 24
<212> TYPE: PRT
<213> ORGANISM: Homo sapiens

<400> SEQUENCE: 3

Thr Lys Cys Leu Arg Arg Glu Ala Pro Arg Trp Asp Ala Pro Leu Arg
1               5                   10                  15

Asp Pro Ala Leu Arg Gln Leu Leu
            20

<210> SEQ ID NO 4
<211> LENGTH: 593
<212> TYPE: PRT
<213> ORGANISM: Homo sapiens

<400> SEQUENCE: 4

Met Trp Thr Leu Val Ser Trp Val Ala Leu Thr Ala Gly Leu Val Ala
1               5                   10                  15

Gly Thr Arg Cys Pro Asp Gly Gln Phe Cys Pro Val Ala Cys Cys Leu
                20                  25                  30

Asp Pro Gly Gly Ala Ser Tyr Ser Cys Cys Arg Pro Leu Leu Asp Lys
            35                  40                  45

Trp Pro Thr Thr Leu Ser Arg His Leu Gly Gly Pro Cys Gln Val Asp
        50                  55                  60

Ala His Cys Ser Ala Gly His Ser Cys Ile Phe Thr Val Ser Gly Thr
65                  70                  75                  80

Ser Ser Cys Cys Pro Phe Pro Glu Ala Val Ala Cys Gly Asp Gly His
                85                  90                  95

His Cys Cys Pro Arg Gly Phe His Cys Ser Ala Asp Gly Arg Ser Cys
```

```
              100                 105                 110
Phe Gln Arg Ser Gly Asn Asn Ser Val Gly Ala Ile Gln Cys Pro Asp
            115                 120                 125
Ser Gln Phe Glu Cys Pro Asp Phe Ser Thr Cys Cys Val Met Val Asp
            130                 135                 140
Gly Ser Trp Gly Cys Cys Pro Met Pro Gln Ala Ser Cys Cys Glu Asp
145                 150                 155                 160
Arg Val His Cys Cys Pro His Gly Ala Phe Cys Asp Leu Val His Thr
                165                 170                 175
Arg Cys Ile Thr Pro Thr Gly Thr His Pro Leu Ala Lys Lys Leu Pro
            180                 185                 190
Ala Gln Arg Thr Asn Arg Ala Val Ala Leu Ser Ser Val Met Cys
            195                 200                 205
Pro Asp Ala Arg Ser Arg Cys Pro Asp Gly Ser Thr Cys Cys Glu Leu
210                 215                 220
Pro Ser Gly Lys Tyr Gly Cys Cys Pro Met Pro Asn Ala Thr Cys Cys
225                 230                 235                 240
Ser Asp His Leu His Cys Cys Pro Gln Asp Thr Val Cys Asp Leu Ile
                245                 250                 255
Gln Ser Lys Cys Leu Ser Lys Glu Asn Ala Thr Thr Asp Leu Leu Thr
            260                 265                 270
Lys Leu Pro Ala His Thr Val Gly Asp Val Lys Cys Asp Met Glu Val
            275                 280                 285
Ser Cys Pro Asp Gly Tyr Thr Cys Cys Arg Leu Gln Ser Gly Ala Trp
            290                 295                 300
Gly Cys Cys Pro Phe Thr Gln Ala Val Cys Cys Glu Asp His Ile His
305                 310                 315                 320
Cys Cys Pro Ala Gly Phe Thr Cys Asp Thr Gln Lys Gly Thr Cys Glu
                325                 330                 335
Gln Gly Pro His Gln Val Pro Trp Met Glu Lys Ala Pro Ala His Leu
            340                 345                 350
Ser Leu Pro Asp Pro Gln Ala Leu Lys Arg Asp Val Pro Cys Asp Asn
            355                 360                 365
Val Ser Ser Cys Pro Ser Ser Asp Thr Cys Cys Gln Leu Thr Ser Gly
370                 375                 380
Glu Trp Gly Cys Cys Pro Ile Pro Glu Ala Val Cys Cys Ser Asp His
385                 390                 395                 400
Gln His Cys Cys Pro Gln Gly Tyr Thr Cys Val Ala Glu Gly Gln Cys
                405                 410                 415
Gln Arg Gly Ser Glu Ile Val Ala Gly Leu Glu Lys Met Pro Ala Arg
            420                 425                 430
Arg Ala Ser Leu Ser His Pro Arg Asp Ile Gly Cys Asp Gln His Thr
            435                 440                 445
Ser Cys Pro Val Gly Gln Thr Cys Cys Pro Ser Leu Gly Gly Ser Trp
            450                 455                 460
Ala Cys Cys Gln Leu Pro His Ala Val Cys Cys Glu Asp Arg Gln His
465                 470                 475                 480
Cys Cys Pro Ala Gly Tyr Thr Cys Asn Val Lys Ala Arg Ser Cys Glu
                485                 490                 495
Lys Glu Val Val Ser Ala Gln Pro Ala Thr Phe Leu Ala Arg Ser Pro
            500                 505                 510
His Val Gly Val Lys Asp Val Glu Cys Gly Glu Gly His Phe Cys His
            515                 520                 525
```

```
Asp Asn Gln Thr Cys Cys Arg Asp Asn Arg Gln Gly Trp Ala Cys Cys
        530                 535                 540

Pro Tyr Arg Gln Gly Val Cys Cys Ala Asp Arg Arg His Cys Cys Pro
545                 550                 555                 560

Ala Gly Phe Arg Cys Ala Ala Arg Gly Thr Lys Cys Leu Arg Arg Glu
                565                 570                 575

Ala Pro Arg Trp Asp Ala Pro Leu Arg Asp Pro Ala Leu Arg Gln Leu
                580                 585                 590

Leu
```

```
<210> SEQ ID NO 5
<211> LENGTH: 13
<212> TYPE: PRT
<213> ORGANISM: Homo sapiens

<400> SEQUENCE: 5

Gln Leu Tyr Glu Asn Lys Pro Arg Arg Pro Tyr Ile Leu
1               5                   10
```

```
<210> SEQ ID NO 6
<211> LENGTH: 44
<212> TYPE: PRT
<213> ORGANISM: Homo sapiens

<400> SEQUENCE: 6

Gln Asp Arg Leu Asp Ala Pro Pro Pro Ala Ala Pro Leu Pro Arg
1               5                   10                  15

Trp Ser Gly Pro Ile Gly Val Ser Trp Gly Leu Arg Ala Ala Ala
                20                  25                  30

Gly Gly Ala Phe Pro Arg Gly Gly Arg Trp Arg Arg
            35                  40
```

```
<210> SEQ ID NO 7
<211> LENGTH: 223
<212> TYPE: PRT
<213> ORGANISM: Homo sapiens

<400> SEQUENCE: 7

Glu Pro His Ser Glu Ser Asn Val Pro Ala Gly His Thr Ile Pro Gln
1               5                   10                  15

Ala His Trp Thr Lys Leu Gln His Ser Leu Asp Thr Ala Leu Arg Arg
                20                  25                  30

Ala Arg Ser Ala Pro Ala Ala Ala Ile Ala Ala Arg Val Ala Gly Gln
            35                  40                  45

Thr Arg Asn Ile Thr Val Asp Pro Arg Leu Phe Lys Lys Arg Arg Leu
50                  55                  60

Arg Ser Pro Arg Val Leu Phe Ser Thr Gln Pro Pro Arg Glu Ala Ala
65                  70                  75                  80

Asp Thr Gln Asp Leu Asp Phe Glu Val Gly Gly Ala Ala Pro Phe Asn
                85                  90                  95

Arg Thr His Arg Ser Lys Arg Ser Ser Ser His Pro Ile Phe His Arg
            100                 105                 110

Gly Glu Phe Ser Val Cys Asp Ser Val Ser Val Trp Val Gly Asp Lys
        115                 120                 125

Thr Thr Ala Thr Asp Ile Lys Gly Lys Glu Val Met Val Leu Gly Glu
    130                 135                 140

Val Asn Ile Asn Asn Ser Val Phe Lys Gln Tyr Phe Phe Glu Thr Lys
```

```
                    145                 150                 155                 160
Cys Arg Asp Pro Asn Pro Val Asp Ser Gly Cys Arg Gly Ile Asp Ser
                165                 170                 175

Lys His Trp Asn Ser Tyr Cys Thr Thr Thr His Thr Phe Val Lys Ala
            180                 185                 190

Leu Thr Met Asp Gly Lys Gln Ala Ala Trp Arg Phe Ile Arg Ile Asp
        195                 200                 205

Thr Ala Cys Val Cys Val Leu Ser Arg Lys Ala Val Arg Arg Ala
    210                 215                 220

<210> SEQ ID NO 8
<211> LENGTH: 692
<212> TYPE: PRT
<213> ORGANISM: Homo sapiens

<400> SEQUENCE: 8

Met Gly Thr Val Ser Ser Arg Arg Ser Trp Trp Pro Leu Pro Leu Leu
1               5                   10                  15

Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300
```

-continued

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
            325                 330                 335

Gly Ala Thr Asn Ala Gln Asp Gln Pro Val Thr Leu Gly Thr Leu Gly
        340                 345                 350

Thr Asn Phe Gly Arg Cys Val Asp Leu Phe Ala Pro Gly Glu Asp Ile
    355                 360                 365

Ile Gly Ala Ser Ser Asp Cys Ser Thr Cys Phe Val Ser Gln Ser Gly
370                 375                 380

Thr Ser Gln Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
530                 535                 540

Ser Met Gly Thr Arg Val His Cys His Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys His Ala Pro Gly Leu Glu Cys
        595                 600                 605

Lys Val Lys Glu His Gly Ile Pro Ala Pro Gln Glu Gln Val Thr Val
610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln
    690

<210> SEQ ID NO 9
<211> LENGTH: 770
<212> TYPE: PRT

<213> ORGANISM: Homo sapiens

<400> SEQUENCE: 9

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
            245                 250                 255

Glu Ala Glu Glu Pro Tyr Glu Glu Ala Thr Glu Arg Thr Thr Ser Ile
        260                 265                 270

Ala Thr Thr Thr Thr Thr Thr Thr Glu Ser Val Glu Glu Val Val Arg
    275                 280                 285

Glu Val Cys Ser Glu Gln Ala Glu Thr Gly Pro Cys Arg Ala Met Ile
        290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
            340                 345                 350

Thr Gln Glu Pro Leu Ala Arg Asp Pro Val Lys Leu Pro Thr Thr Ala
        355                 360                 365

Ala Ser Thr Pro Asp Ala Val Asp Lys Tyr Leu Glu Thr Pro Gly Asp
    370                 375                 380

Glu Asn Glu His Ala His Phe Gln Lys Ala Lys Glu Arg Leu Glu Ala
385                 390                 395                 400

```
Lys His Arg Glu Arg Met Ser Gln Val Met Arg Glu Trp Glu Ala
                405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
        435                 440                 445

Glu Arg Gln Gln Leu Val Glu Thr His Met Ala Arg Val Glu Ala Met
    450                 455                 460

Leu Asn Asp Arg Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
        515                 520                 525

Gln Val Met Thr His Leu Arg Val Ile Tyr Glu Arg Met Asn Gln Ser
    530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
            580                 585                 590

Leu Met Pro Ser Leu Thr Glu Thr Lys Thr Thr Val Glu Leu Leu Pro
        595                 600                 605

Val Asn Gly Glu Phe Ser Leu Asp Asp Leu Gln Pro Trp His Ser Phe
    610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
            660                 665                 670

Ala Glu Phe Arg His Asp Ser Gly Tyr Glu Val His His Gln Lys Leu
        675                 680                 685

Val Phe Phe Ala Glu Asp Val Gly Ser Asn Lys Gly Ala Ile Ile Gly
    690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
        755                 760                 765

Gln Asn
    770

<210> SEQ ID NO 10
<211> LENGTH: 40
<212> TYPE: PRT
<213> ORGANISM: Homo sapiens

<400> SEQUENCE: 10
```

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val
            35              40

<210> SEQ ID NO 11
<211> LENGTH: 42
<212> TYPE: PRT
<213> ORGANISM: Homo sapiens

<400> SEQUENCE: 11

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala
            35                  40
```